United States Patent
Sakaguchi et al.

(10) Patent No.: US 7,550,483 B2
(45) Date of Patent: Jun. 23, 2009

(54) AMORPHOUS SALT OF 4-(3-CHLORO-4-(CYCLOPROPYLAMINO CARBONYL)AMINOPHENOXY)-7-METHOXY-6-QUINOLINECARBOXAMIDE AND PROCESS FOR PREPARING THE SAME

(75) Inventors: Takahisa Sakaguchi, Tsukuba (JP); Akihiko Tsuruoka, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 398 days.

(21) Appl. No.: 11/472,372

(22) Filed: Jun. 22, 2006

(65) Prior Publication Data

US 2007/0004773 A1    Jan. 4, 2007

Related U.S. Application Data

(60) Provisional application No. 60/693,044, filed on Jun. 23, 2005.

(51) Int. Cl.
*A61K 31/44* (2006.01)
*C07D 215/38* (2006.01)

(52) U.S. Cl. .......... 514/313; 546/153; 546/159

(58) Field of Classification Search ........ 546/153, 546/159; 514/313
See application file for complete search history.

(56) References Cited

U.S. PATENT DOCUMENTS 7,253,286 B2 *  8/2007  Funahashi et al. ........... 546/153

| | | |
|---|---|---|
| 2004/0053908 A1 | 3/2004 | Funahashi et al. |
| 2004/0242506 A1 | 12/2004 | Barges Causeret et al. |
| 2004/0253205 A1 | 12/2004 | Yamamoto et al. |
| 2007/0004773 A1 | 1/2007 | Sakaguchi et al. |
| 2007/0078159 A1 * | 4/2007 | Matsushima .......... 514/312 |
| 2007/0117842 A1 * | 5/2007 | Arimoto et al. ........ 514/312 |

FOREIGN PATENT DOCUMENTS

| JP | 1-022874 A1 | 1/1989 |
|---|---|---|
| JP | 64-22874 A | 1/1989 |
| JP | 2001-131071 A | 5/2001 |
| JP | 2005-501074 A | 1/2005 |
| WO | WO-02/32872 A1 | 4/2002 |
| WO | WO-03/013529 A1 | 2/2003 |
| WO | WO-2004/080462 A1 | 9/2004 |
| WO | WO-2004/101526 A1 | 11/2004 |
| WO | WO-2005/044788 A1 | 5/2005 |
| WO | WO-2005/063713 A1 | 7/2005 |
| WO | WO2006/030826 A1 | 3/2006 |
| WO | WO-2006/030826 A1 | 3/2006 |

OTHER PUBLICATIONS

John K. Haleblian., "Characterization of Habits and Crystalline Modification of Solids and Their Pharmaceutical Applications," Journal of Pharmaceutical Sciences, vol. 64, No. 8, Aug. 1975, pp. 1269-1288.

Office Action dated Sep. 23, 2008, issued in copending U.S. Appl. No. 10/577,531.

* cited by examiner

*Primary Examiner*—D. Margaret Seaman
(74) *Attorney, Agent, or Firm*—Birch, Stewart, Kolasch & Birch, LLP

(57) ABSTRACT

An amorphous form of a salt of 4-(3-chloro-4-(cyclopropylaminocarbonyl)aminophenoxy)-7-methoxy-6-quinolinecarboxamide.

6 Claims, 16 Drawing Sheets

AMORPHOUS SALT OF 4-(3-CHLORO-4-(CYCLOPROPYLAMINO CARBONYL)AMINOPHENOXY)-7-METHOXY-6-QUINOLINECARBOXAMIDE AND PROCESS FOR PREPARING THE SAME

CROSS-REFERENCE TO RELATED APPLICATION

This application claims the benefit of U.S. Provisional Application No. 60/693,044 filed on Jun. 23, 2005, which is incorporated herein by reference in its entirety.

BACKGROUND OF THE INVENTION

1. Field of the Invention

The present invention relates to amorphous forms of salts of 4-(3-chloro-4-(cyclopropylaminocarbonyl)aminophenoxy)-7-methoxy-6-quinolinecarboxamide and processes for preparing the same.

2. Related Background Art 4-(3-Chloro-4-(cyclopropylaminocarbonyl)aminophenoxy)-7-methoxy-6-quinolinecarboxamide (additional name: 4-[3-chloro-4-(N'-cyclopropylureido)phenoxy]-7-methoxyquinoline-6-carboxamide) is known to exhibit an excellent angiogenesis inhibition as a free-form product, as described in Example 368 of Patent Document 1. 4-(3-Chloro-4-(cyclopropylaminocarbonyl)aminophenoxy)-7-methoxy-6-quinolinecarboxamide is also known to exhibit a strong inhibitory action for c-Kit kinase (Non-Patent Document 1, Patent Document 2).

However, there has been a long-felt need for the provision of an angiogenesis inhibitor or c-Kit kinase inhibitor that has high usability as a medicament and superior characteristics in terms of physical properties and pharmacokinetics in comparison with the free-form product of 4-(3-chloro-4-(cyclopropylaminocarbonyl)aminophenoxy)-7-methoxy-6-quinolinecarboxamide.

[Patent Document 1] WO02/32872

[Patent Document 2] WO2004/080462

[Non-patent Document 1] 95th Annual Meeting Proceedings, AACR (American Association for Cancer Research), Volume 45, Page 1070-1071, 2004.

SUMMARY OF THE INVENTION

It is an object of the present invention to provide amorphous forms of salts of 4-(3-chloro-4-(cyclopropylaminocarbonyl)aminophenoxy)-7-methoxy-6-quinolinecarboxamide which have high usability as medicaments and processes for preparing the same.

In order to achieve the above object, the present invention provides the followings:

<1> an amorphous form of a salt of 4-(3-chloro-4-(cyclopropylaminocarbonyl)aminophenoxy)-7-methoxy-6-quinolinecarboxamide;

<2> an amorphous form of 4-(3-chloro-4-(cyclopropylaminocarbonyl)aminophenoxy)-7-methoxy-6-quinolinecarboxamide methanesulfonate;

<3> an amorphous form of 4-(3-chloro-4-(cyclopropylaminocarbonyl)aminophenoxy)-7-methoxy-6-quinolinecarboxamide ethanesulfonate;

<4> a process for preparing an amorphous form of 4-(3-chloro-4-(cyclopropylaminocarbonyl)aminophenoxy)-7-methoxy-6-quinolinecarboxamide methanesulfonate, characterized by dissolving a crystalline form of 4-(3-chloro-4-(cyclopropylaminocarbonyl)aminophenoxy)-7-methoxy-6-quinolinecarboxamide methanesulfonate in an alcohol and water;

<5> a process for preparing an amorphous form of 4-(3-chloro-4-(cyclopropylaminocarbonyl)aminophenoxy)-7-methoxy-6-quinolinecarboxamide ethanesulfonate, characterized by dissolving a crystalline form of 4-(3-chloro-4-(cyclopropylaminocarbonyl)aminophenoxy)-7-methoxy-6-quinolinecarboxamide ethanesulfonate in an alcohol and water;

<6> a pharmaceutical composition comprising an amorphous compound according to any one of <1> to <3>;

<7> a preventing or therapeutic agent for a disease for which angiogenesis inhibition is effective, comprising an amorphous compound according to any one of <1> to <3>;

<8> an angiogenesis inhibitor comprising an amorphous compound according to any one of <1> to <3>;

<9> an anti-tumor agent comprising an amorphous compound according to any one of <1> to <3>;

<10> an anti-tumor agent according to <9>, wherein the tumor is pancreatic cancer, gastric cancer, colorectal cancer, breast cancer, prostate cancer, pulmonary cancer, renal cancer, brain tumor, blood cancer or ovarian cancer;

<11> a therapeutic agent for angioma comprising an amorphous compound according to any one of <1> to <3>;

<12> a cancer metastasis inhibitor comprising an amorphous compound according to any one of <1> to <3>;

<13> a method for preventing or treating a disease for which angiogenesis inhibition is effective, comprising administering a patient a pharmacologically effective amount of an amorphous compound according to any one of <1> to <3>;

<14> use of an amorphous compound according to any one of <1> to <3> for the manufacture of a preventing or therapeutic agent for a disease for which angiogenesis inhibition is effective;

<15> a therapeutic agent for retinal neovascularization, comprising an amorphous compound according to any one of <1> to <3>;

<16> a therapeutic agent for diabetic retinopathy, comprising an amorphous compound according to any one of <1> to <3>;

<17> a therapeutic agent for an inflammatory disease, comprising an amorphous compound according to any one of <1> to <3>;

<18> a therapeutic agent for an inflammatory disease according to <17>, wherein the inflammatory disease is deformant arthritis, rheumatoid arthritis, psoriasis or delayed hypersensitivity reaction; and <19> a therapeutic agent for atherosclerosis, comprising an amorphous compound according to any one of <1> to <3>. The present invention also provides the followings:

<20> a c-Kit kinase inhibitor, comprising an amorphous compound according to any one of <1> to <3>;

<21> an anti-cancer agent for treating a cancer expressing excessive c-Kit kinase or a mutant c-Kit kinase, comprising an amorphous compound according to any one of <1> to <3>;

<22> an anti-cancer agent according to <21>, wherein the cancer expressing excessive c-Kit kinase or a mutant c-Kit kinase is acute myelogenous leukemia, mast cell leukemia, a small cell lung cancer, GIST, a testicular tumor, an ovarian cancer, a breast cancer, a brain tumor, neuroblastoma or a colorectal cancer;

<23> an anti-cancer agent according to <21>, wherein the cancer expressing excessive c-Kit kinase or a mutant c-Kit kinase is acute myelogenous leukemia, a small cell lung cancer or GIST;

<24> an anti-cancer agent according to any one of <21> to <23>, which is applied to a patient for which a cancer expressing excessive c-Kit kinase or a mutant c-Kit kinase is identified;

<25> a therapeutic agent for mastocytosis, allergy or asthma, comprising an amorphous compound according to any one of <1> to <3>;

<26> a method for treating a cancer, comprising administering to a patient suffering from a cancer expressing excessive c-Kit kinase or a mutant c-Kit kinase, a pharmacologically effective dose of an amorphous compound according to any one of <1> to <3>;

<27> a method according to <26>, wherein the cancer expressing excessive c-Kit kinase or a mutant c-Kit kinase is acute myelogenous leukemia, mast cell leukemia, a small cell lung cancer, GIST, a testicular tumor, an ovarian cancer, a breast cancer, a brain tumor, neuroblastoma or a colorectal cancer;

<28> a method according to <26>, wherein the cancer expressing excessive c-Kit kinase or a mutant c-Kit kinase is acute myelogenous leukemia, a small cell lung cancer or GIST;

<29> a method for treating a cancer, comprising the steps of:

extracting cancer cells from a patient suffering from a cancer;

confirming that the cancer cells are expressing excessive c-Kit kinase or a mutant c-Kit kinase; and administering to the patient, a pharmacologically effective dose of a c-Kit kinase inhibitor according to <20>;

<30> a method for treating mastocytosis, allergy, or asthma, comprising administering to a patient suffering from the disease, a pharmacologically effective dose of a c-Kit kinase inhibitor according to <20>;

<31> a method for inhibiting c-Kit kinase activity, comprising applying to a cell expressing excessive c-Kit kinase or a mutant c-Kit kinase, a pharmacologically effective dose of a c-Kit kinase inhibitor according to <20>;

<32> use of a c-Kit kinase inhibitor according to <20> for the manufacture of an anti-cancer agent for treating a cancer expressing excessive c-Kit kinase or a mutant c-Kit kinase;

<33> use according to <32>, wherein the cancer expressing excessive c-Kit kinase or a mutant c-Kit kinase is acute myelogenous leukemia, mast cell leukemia, a small cell lung cancer, GIST, a testicular tumor, an ovarian cancer, a breast cancer, a brain tumor, neuroblastoma or a colorectal cancer;

<34> use according to <32>, wherein the cancer expressing excessive c-Kit kinase or a mutant c-Kit kinase is acute myelogenous leukemia, a small cell lung cancer or GIST; and <35> use of a c-Kit kinase inhibitor according to <20> for the manufacture of a therapeutic agent for mastocytosis, allergy or asthma.

The amorphous form of the salt of 4-(3-chloro-4-(cyclopropylaminocarbonyl)aminophenoxy)-7-methoxy-6-quinolinecarboxamide (hereunder, referred to as "carboxamide") according to the present invention is extremely useful as an angiogenesis inhibitor or a c-Kit kinase inhibitor.

DESCRIPTION OF THE PREFERRED EMBODIMENTS

Figure 1:
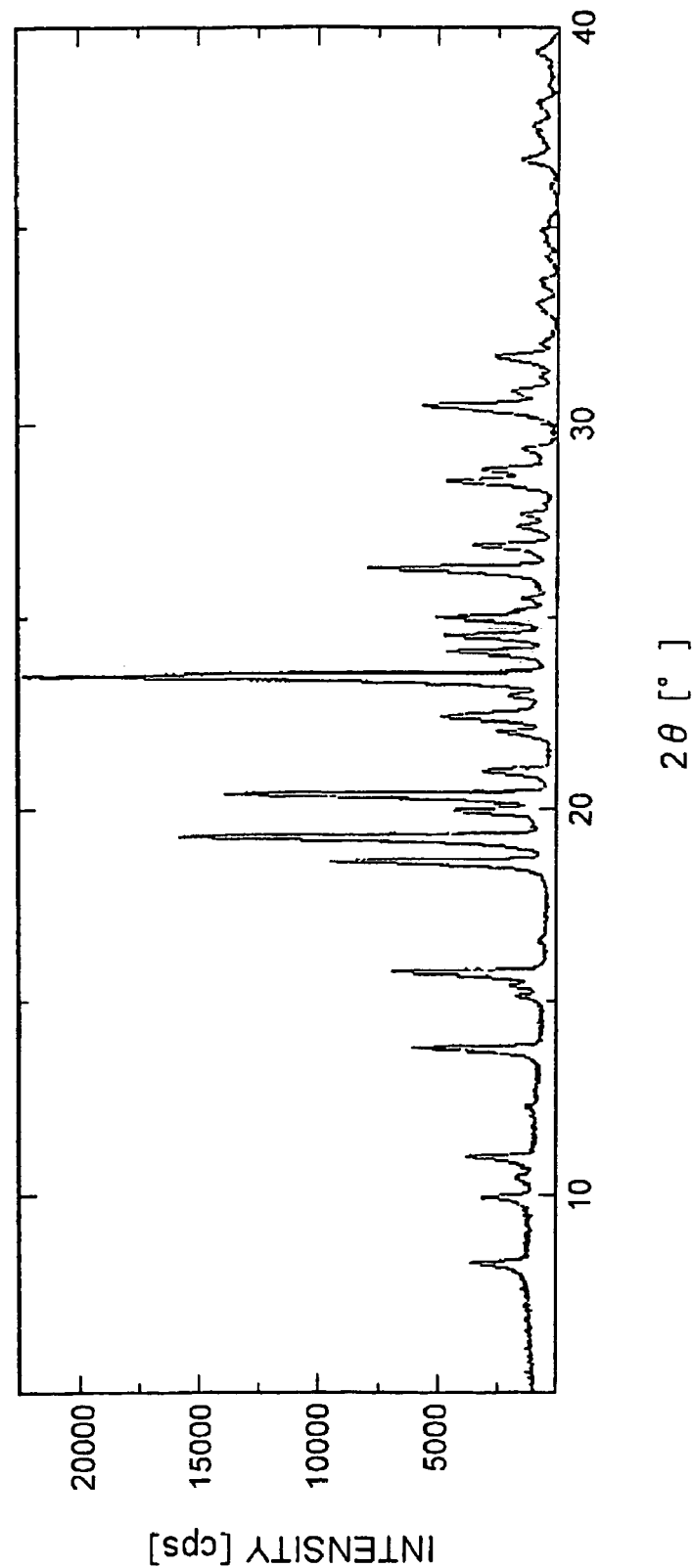
FIG. 1 is a figure illustrating a powder X-ray diffraction pattern for a crystalline form of the free form of the carboxamide obtained in Reference Example 1.
Figure 2:
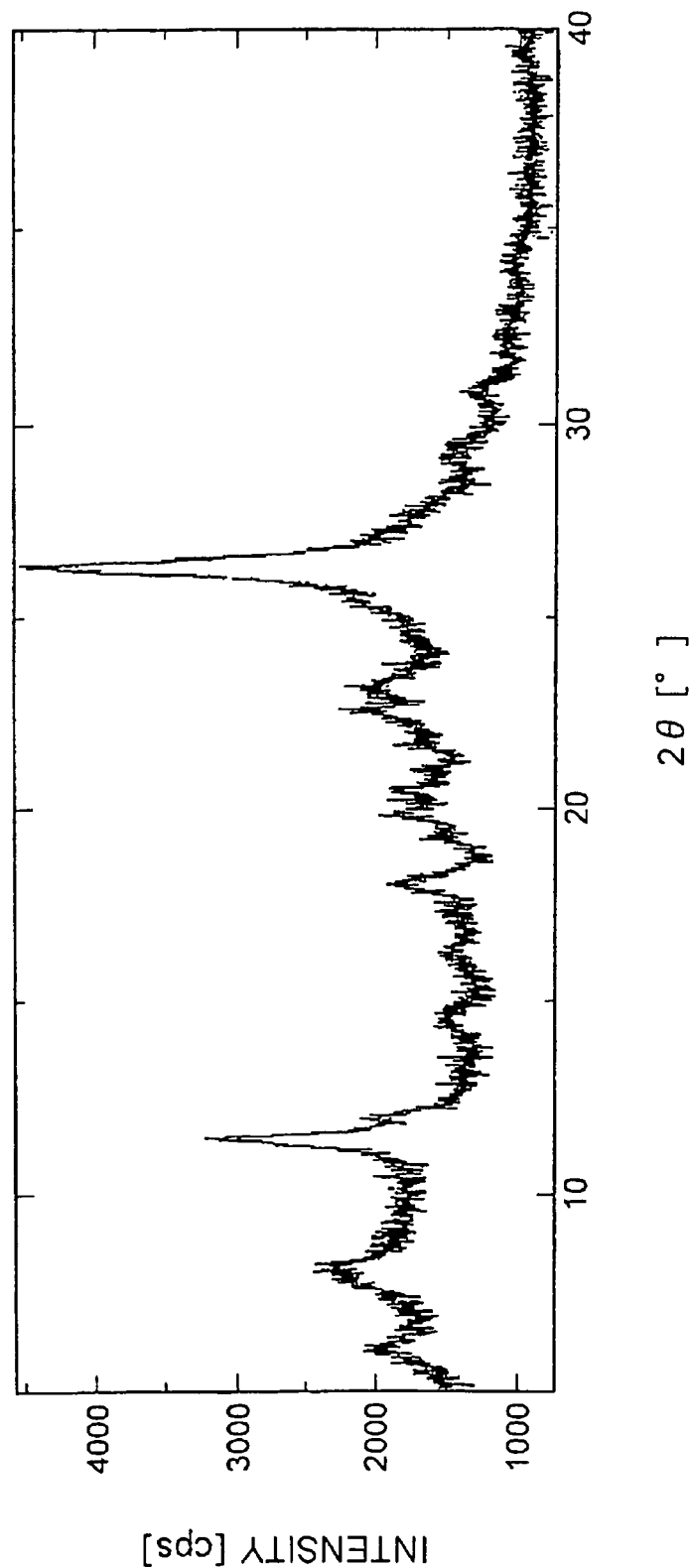
FIG. 2 is a figure illustrating a powder X-ray diffraction pattern for a crystalline form of the hydrochloride of the carboxamide obtained in Reference Example 4.
Figure 3:
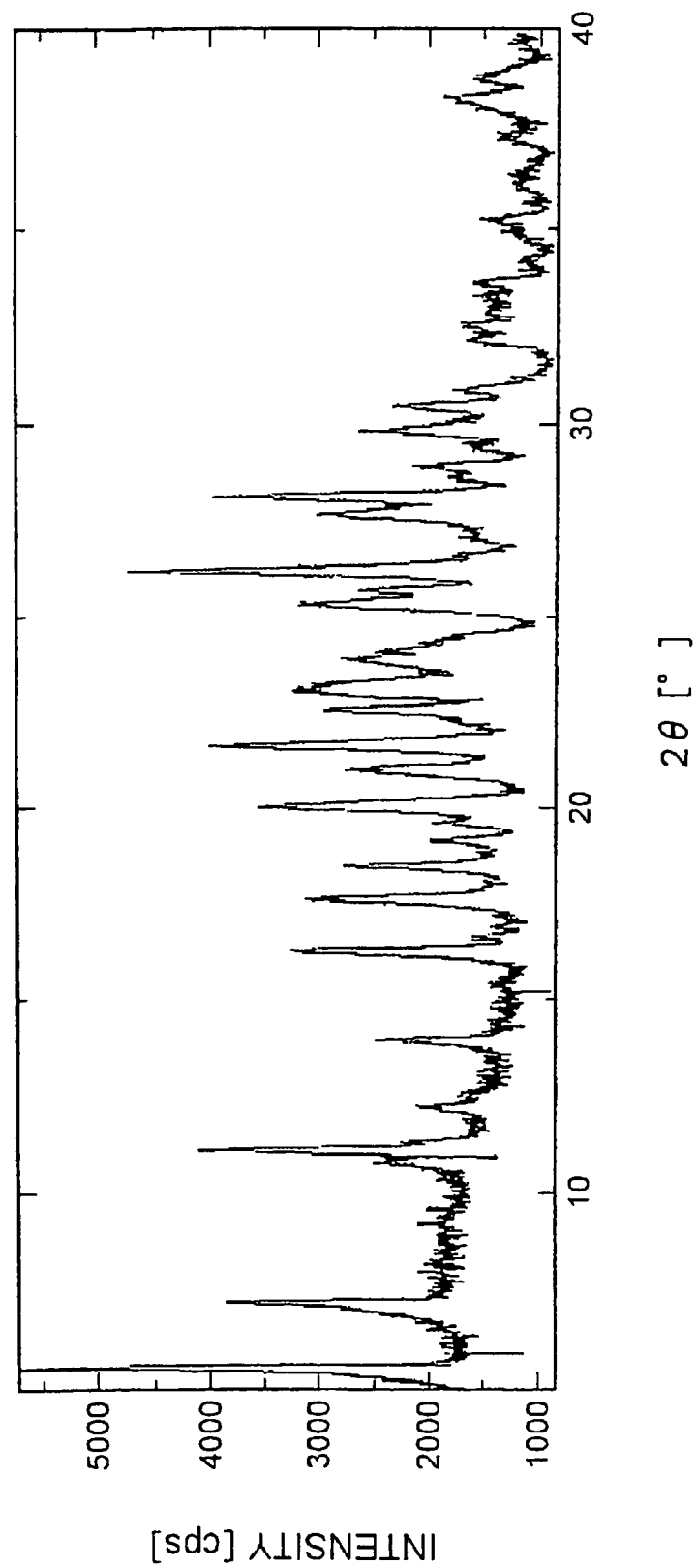
FIG. 3 is a figure illustrating a powder X-ray diffraction pattern for a crystalline form of the hydrobromide of the carboxamide obtained in Reference Example 5.
Figure 4:
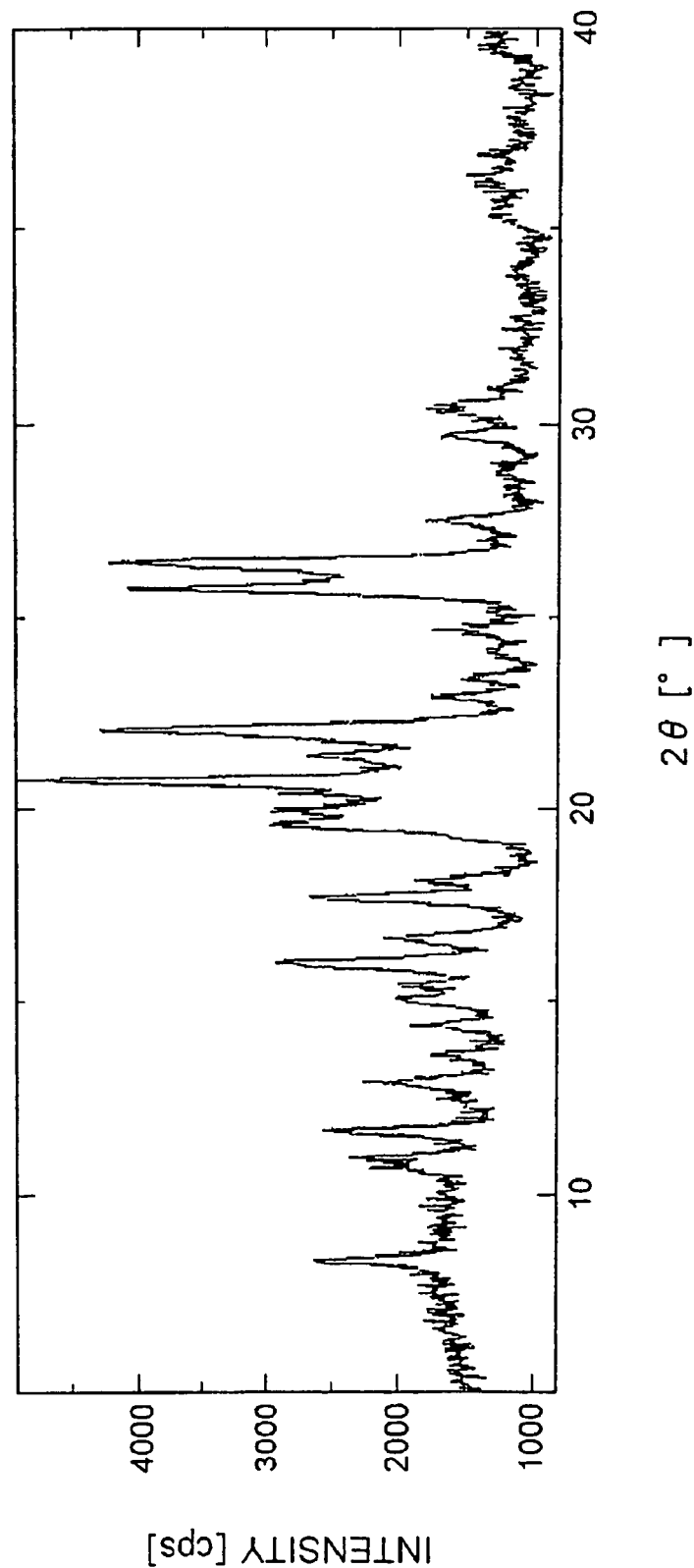
FIG. 4 is a figure illustrating a powder X-ray diffraction pattern of a crystalline form of the p-toluenesulfonate of the carboxamide obtained in Reference Example 6.
Figure 5:
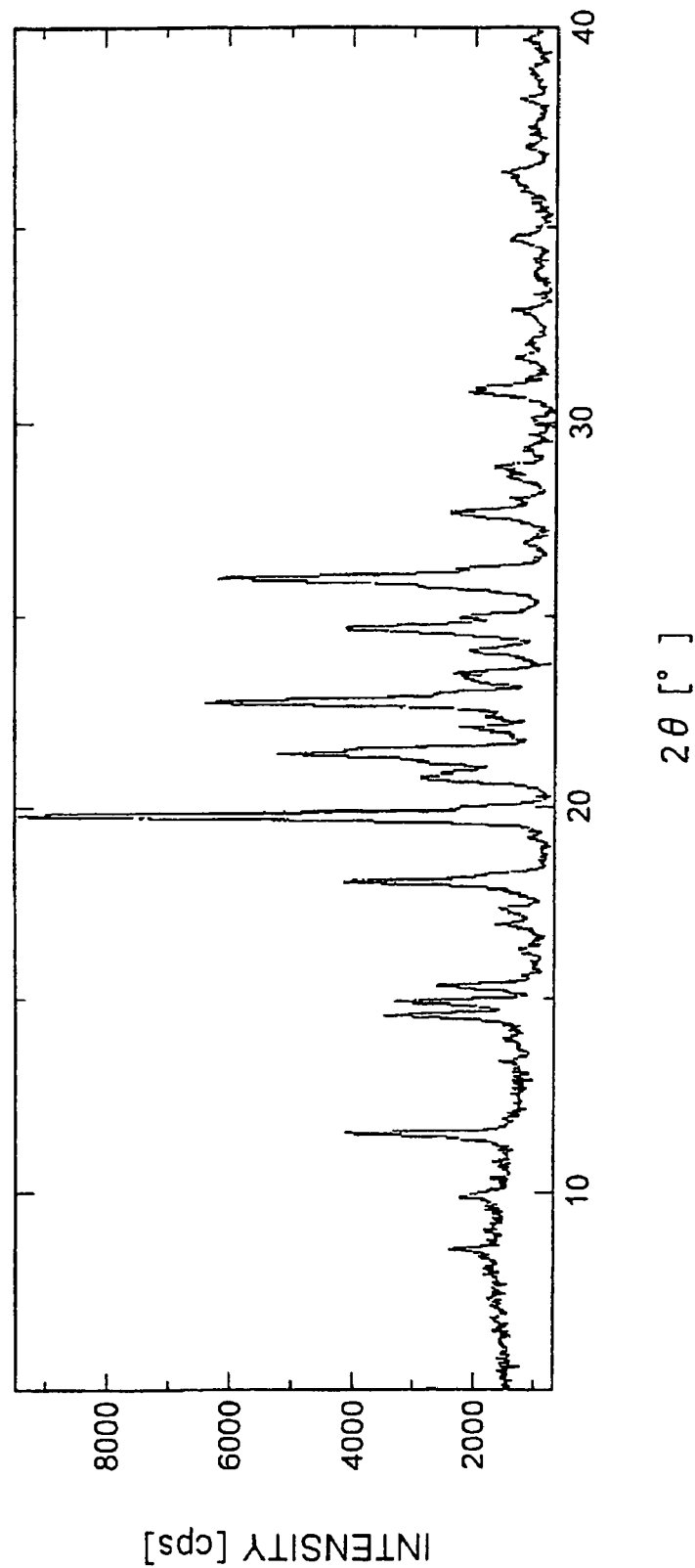
FIG. 5 is a figure illustrating a powder X-ray diffraction pattern for a crystalline form of the sulfate of the carboxamide obtained in Reference Example 7.
Figure 6:
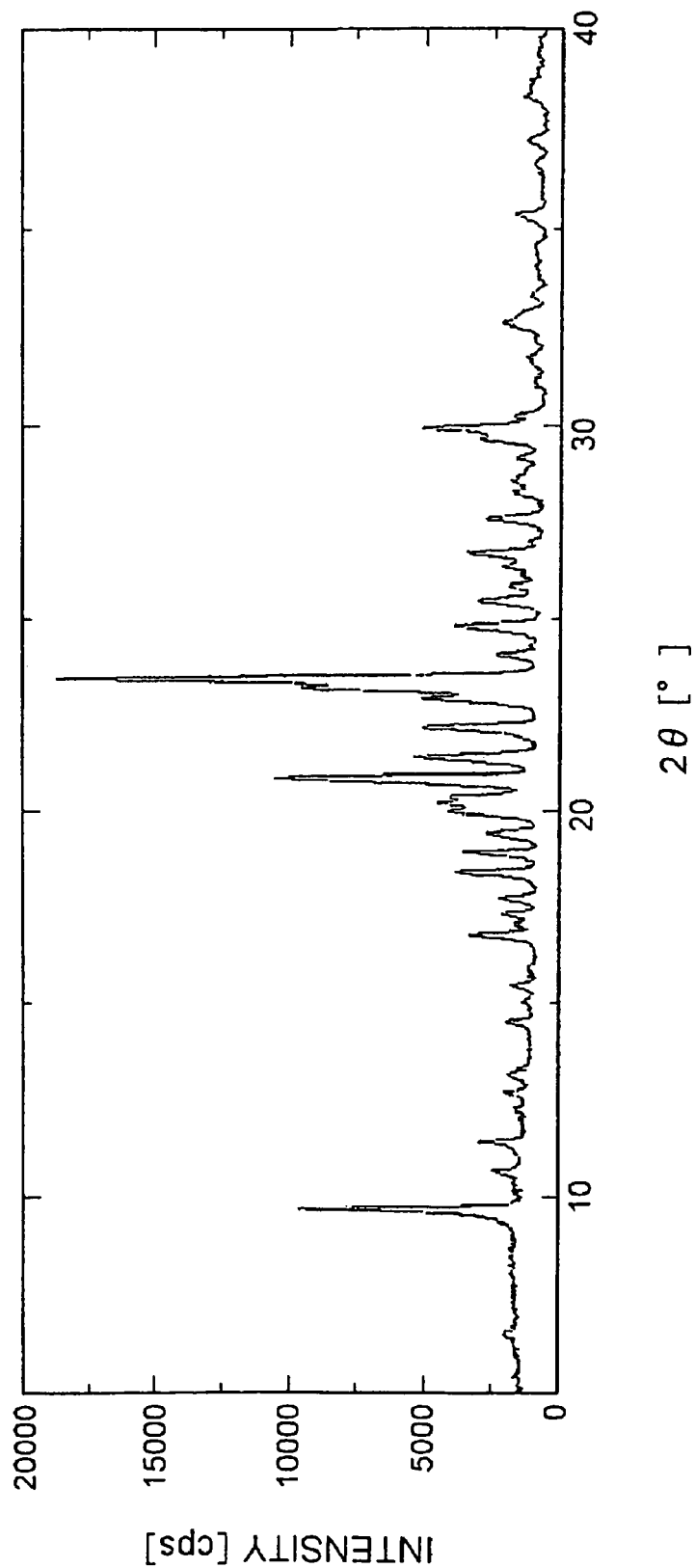
FIG. 6 is a figure illustrating a powder X-ray diffraction pattern for a crystalline form of the methanesulfonate of the carboxamide (Form A) obtained in Reference Example 8.
Figure 7:
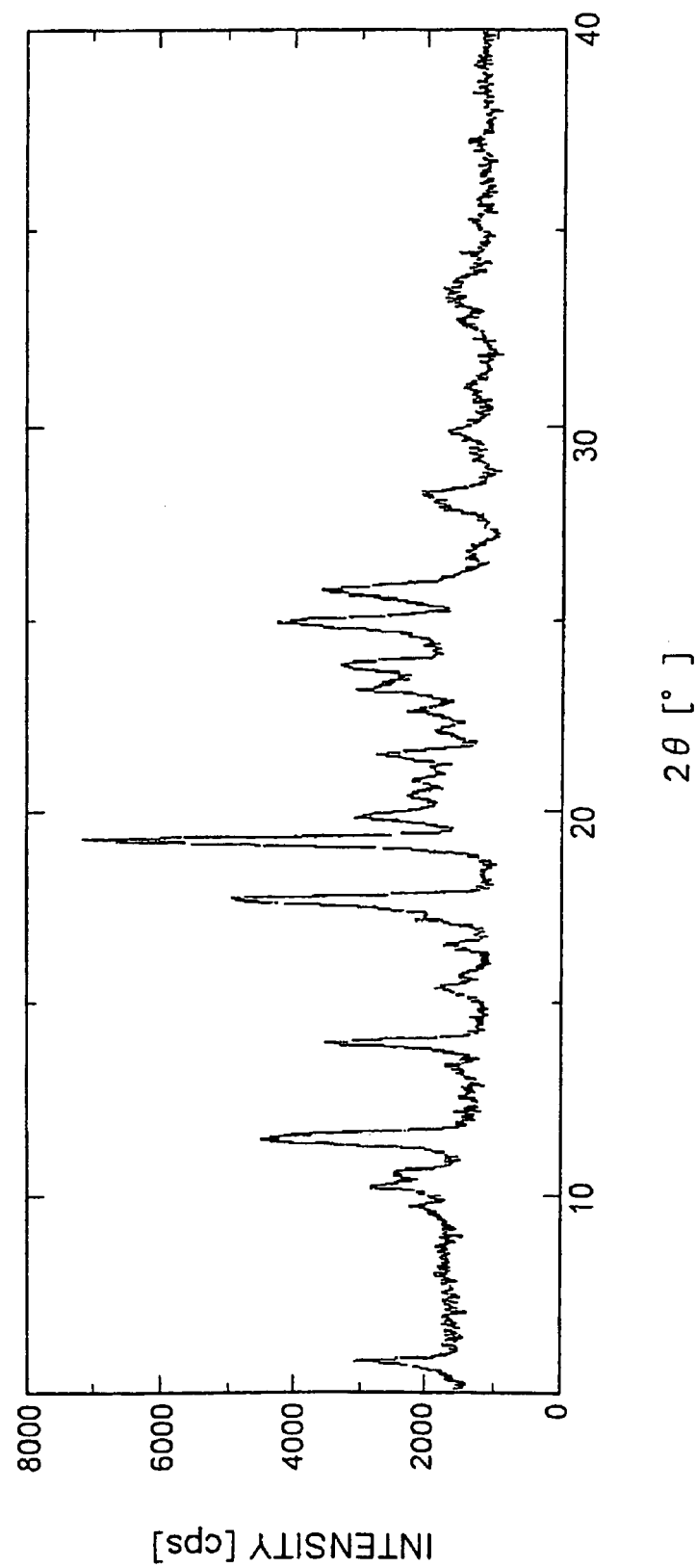
FIG. 7 is a figure illustrating a powder X-ray diffraction pattern for a crystalline form of the methanesulfonate of the carboxamide (Form B) obtained in Reference Example 9.
Figure 8:
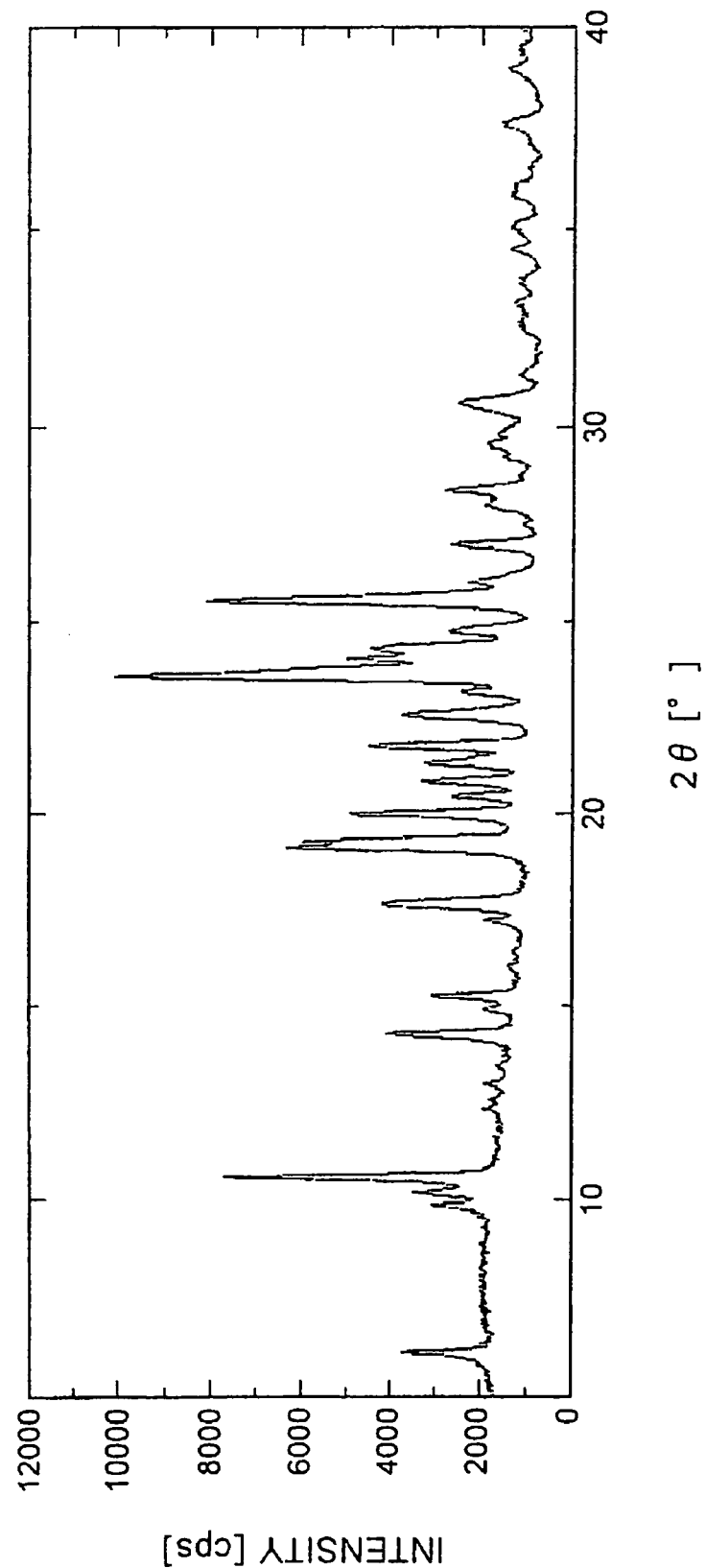
FIG. 8 is a figure illustrating a powder X-ray diffraction pattern for a crystalline form of the methanesulfonate of the carboxamide (Form C) obtained in Reference Example 10.
Figure 9:
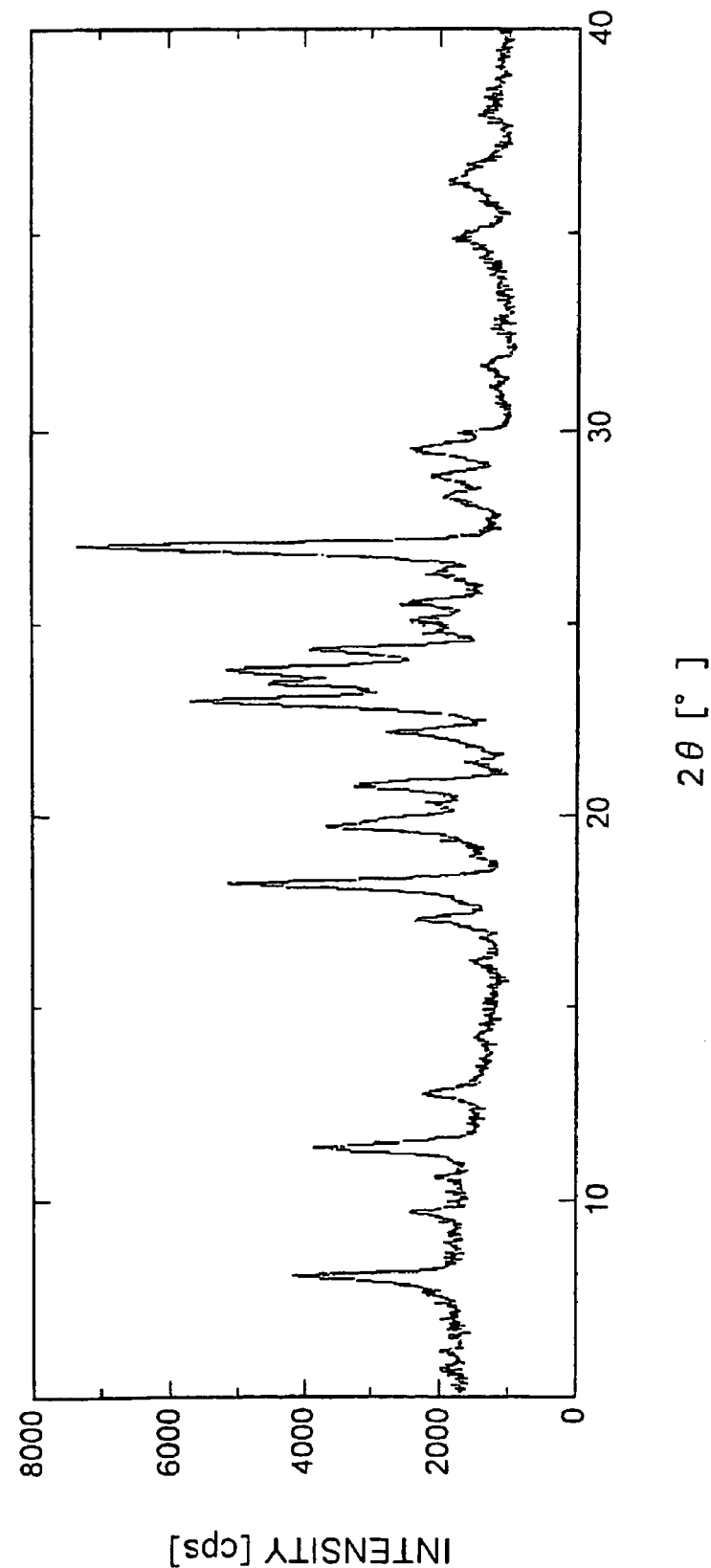
FIG. 9 is a figure illustrating a powder X-ray diffraction pattern for a crystalline form of the hydrate of the methanesulfonate of the carboxamide (Form F) obtained in Reference Example 12.
Figure 10:
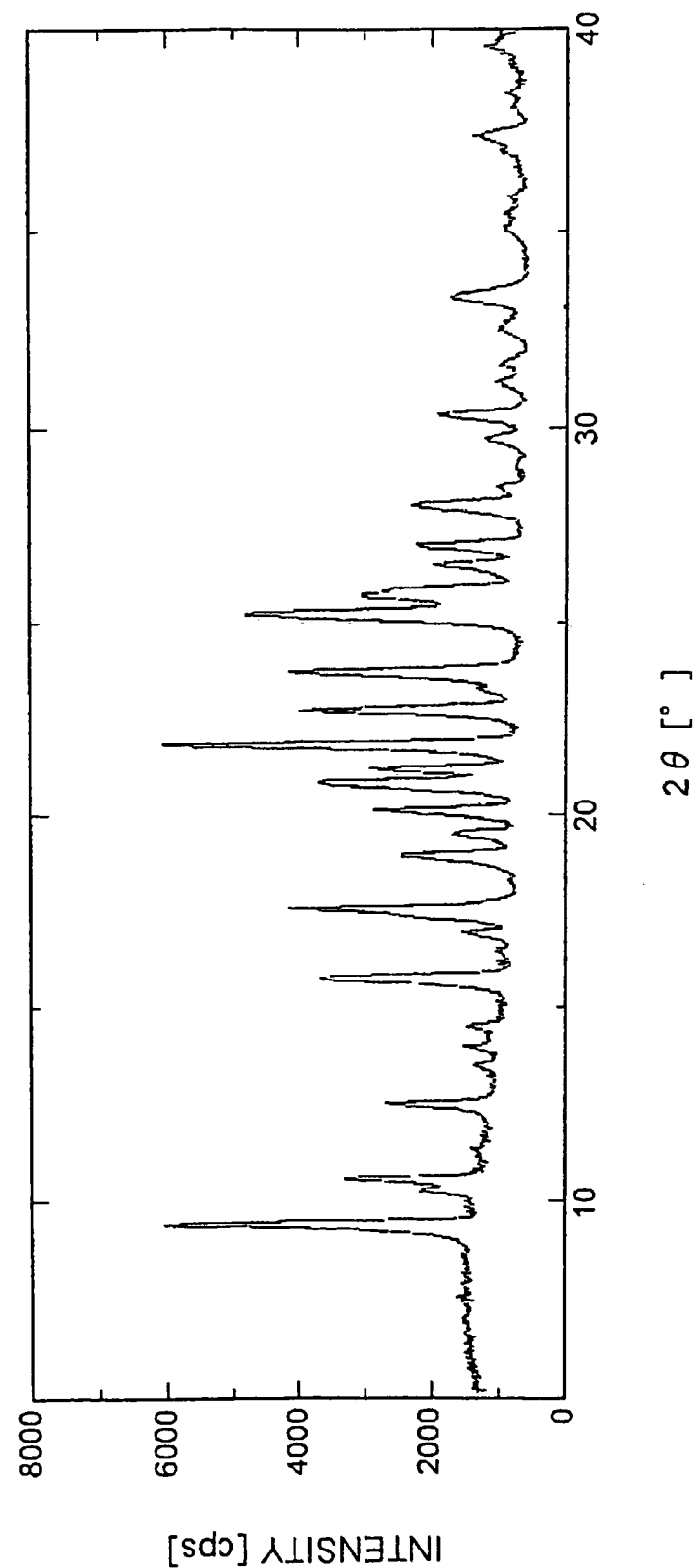
FIG. 10 is a figure illustrating a powder X-ray diffraction pattern for a crystalline form of the acetic acid solvate for the methanesulfonate of the carboxamide (Form I) obtained in Reference Example 13.
Figure 11:
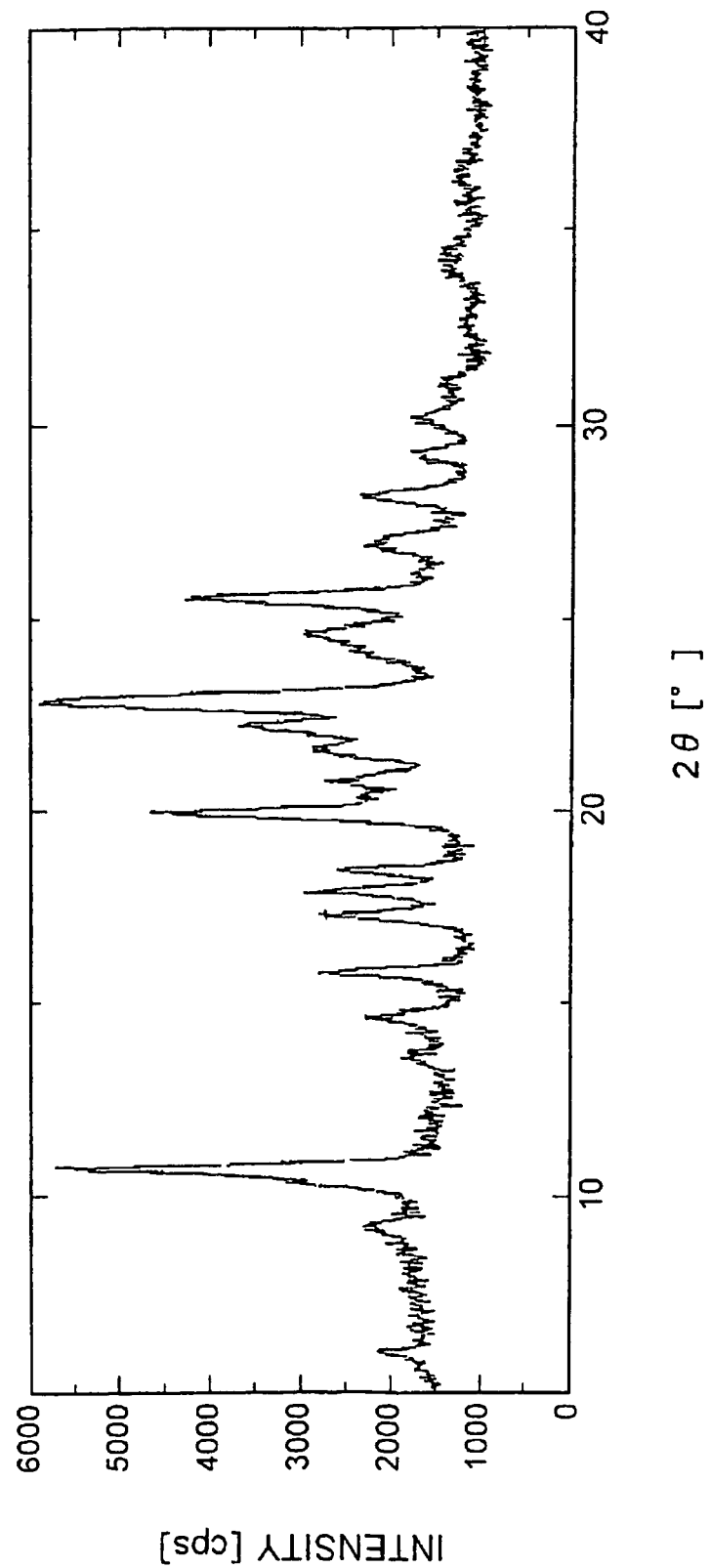
FIG. 11 is a figure illustrating a powder X-ray diffraction pattern for a crystalline form of the ethanesulfonate of the carboxamide (Form α) obtained in Reference Example 14.
Figure 12:
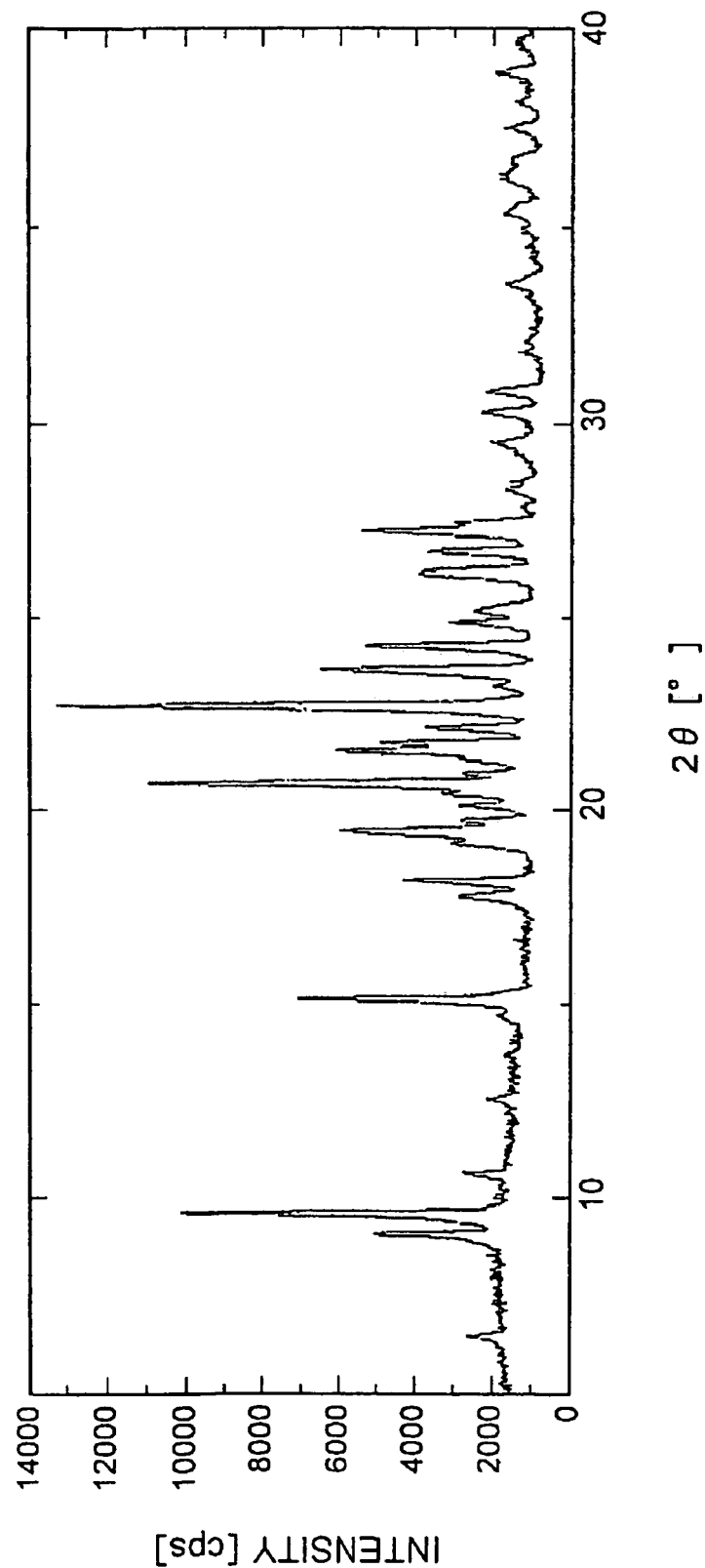
FIG. 12 is a figure illustrating a powder X-ray diffraction pattern for a crystalline form of the ethanesulfonate of the carboxamide (Form β) obtained in Reference Example 15.
Figure 13:
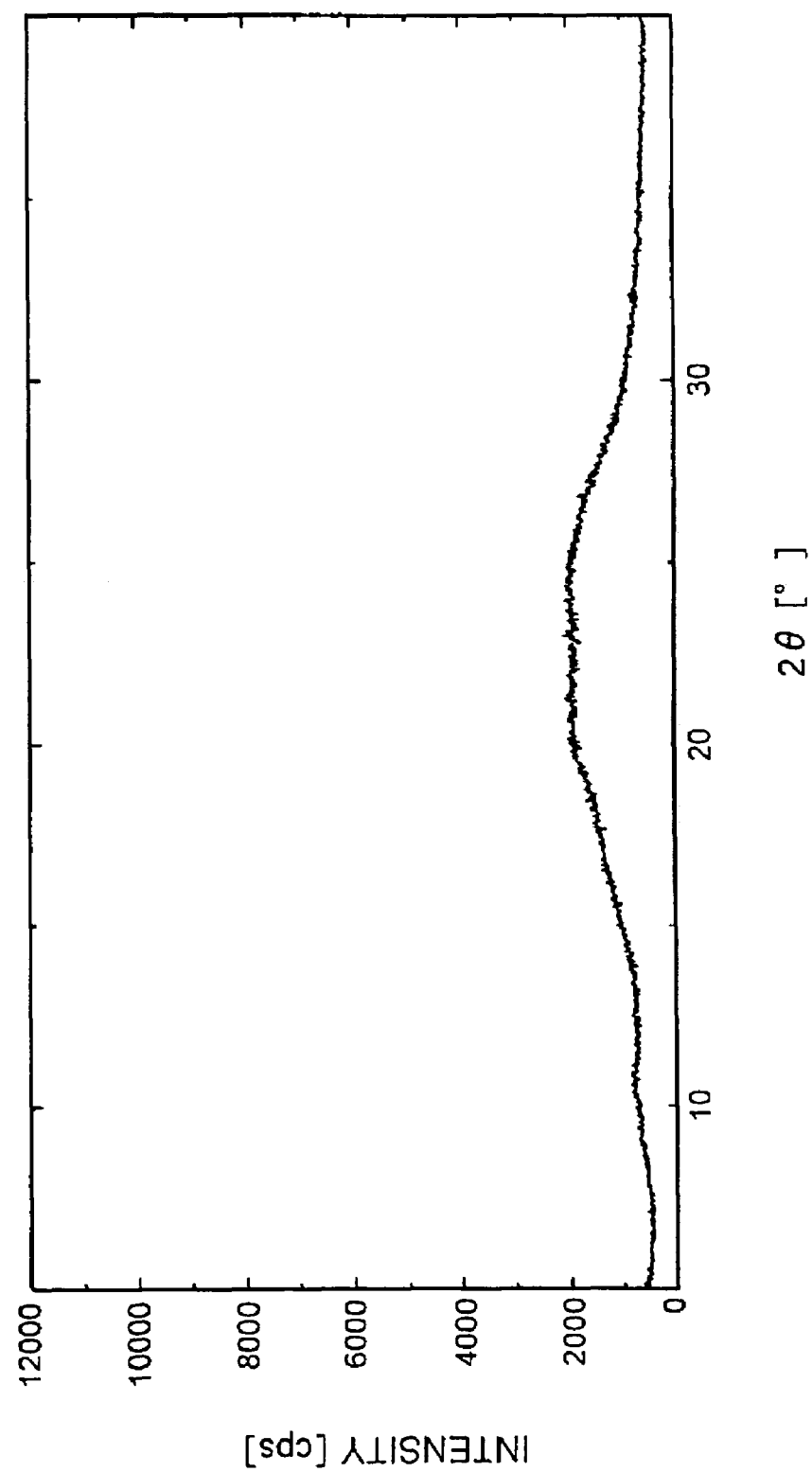
FIG. 13 is a figure illustrating a powder X-ray diffraction pattern for an amorphous form of the methanesulfonate of the carboxamide obtained in Example 1.
Figure 14:
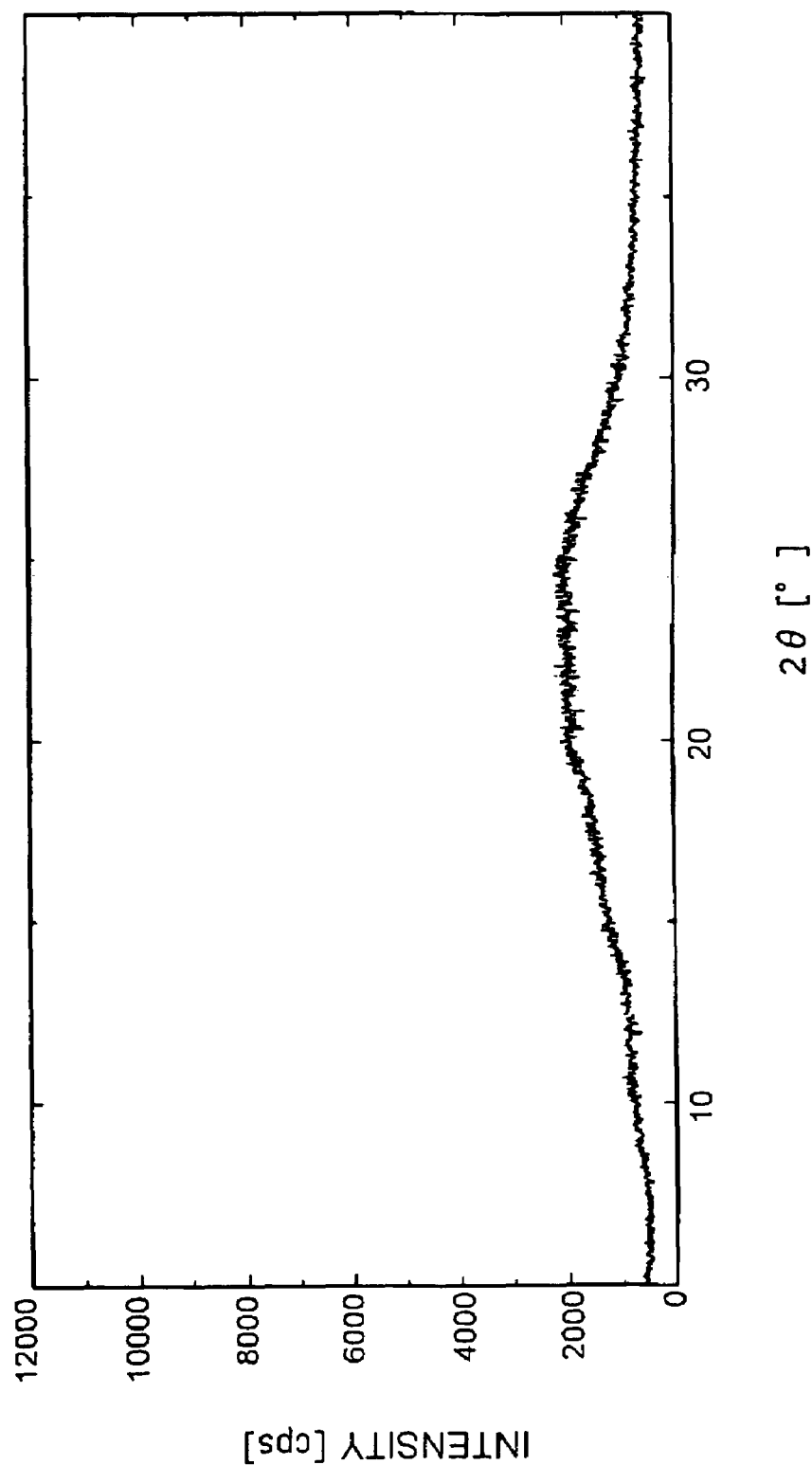
FIG. 14 is a figure illustrating a powder X-ray diffraction pattern for an amorphous form of the ethanesulfonate of the carboxamide obtained in Example 2.

Hereunder, the present invention is described in detail.

As examples of the salt of 4-(3-chloro-4-(cyclopropylaminocarbonyl)aminophenoxy)-7-methoxy-6-quinolinecarboxamide (hereunder, referred to as "carboxamide") according to the present invention, methanesulfonate, ethanesulfonate, p-toluenesulfonate, hydrochloride, hydrobromide, sulfate, tartrate and phosphate may be mentioned.

The salt of the carboxamide according to the present invention can be prepared by ordinary methods (for example, by mixing the carboxamide and the corresponding acid at a suitable ratio in the presence or absence of a solvent). In this connection, in addition to the method described in WO 02/32872, the carboxamide can also be prepared by the method described in Reference Examples 1 to 3 below.

The crystalline form of the salt of the carboxamide can be prepared by the method described in Reference Examples 4 to 16 below.

The amorphous form of the salt of the carboxamide can be prepared by the method described in General Process for Preparation and Examples 1 and 2 below.

[General Process for Preparation]

The amorphous form of the salt of the carboxamide can be prepared by mixing a crystalline form of a salt of the carboxamide and a solvent to dissolve the crystalline form of the salt of the carboxamide and then lyophilizing the solution. A portion of the solvent may be removed prior to the lyophilization, if necessary.

The solvent used may be alcohols such as methanol, ethanol, 1-propanol, 2-propanol and tert-butanol, ethers such as tetrahydrofuran, acetonitrile and/or water, and preferably alcohols and water.

The amount of the solvent is not particularly restricted, and preferably 10 to 100 fold amount with respect to the substrate.

The time for lyophilization is not particularly restricted, and preferably 1 to 240 hours.

When the amorphous compound of the present invention is to be used as a medicament, it will normally be mixed with suitable additives for use as a formulation. However, the foregoing description does not limit the use of the amorphous compound of the present invention as medicament in the state of intact products.

Such additives may include excipients, binders, lubricants, disintegrators, coloring agents, taste correctives, emulsifiers, surfactants, dissolving aids, suspending agents, isotonizing agents, buffering agents, antiseptics, antioxidants, stabilizers, absorption accelerators and the like which are commonly used in pharmaceuticals, and they may be added in appropriate combinations as desired.

As examples of such excipients there may be mentioned lactose, white soft sugar, glucose, corn starch, mannitol, sorbitol, starch, alpha starch, dextrin, crystalline cellulose, soft silicic anhydride, aluminum silicate, calcium silicate, magnesium aluminometasilicate, calcium hydrogenphosphate, and the like.

As examples of binders there may be mentioned polyvinyl alcohol, methylcellulose, ethylcellulose, gum Arabic, tragacanth, gelatin, shellac, hydroxypropylmethylcellulose, hydroxypropylcellulose, carboxymethylcellulose sodium, polyvinylpyrrolidone, macrogol, and the like.

As examples of lubricants there may be mentioned magnesium stearate, calcium stearate, sodium stearyl fumarate, talc, polyethylene glycol, colloidal silica, and the like.

As examples of disintegrators, there may be mentioned crystalline cellulose, agar, gelatin, calcium carbonate, sodium hydrogencarbonate, calcium citrate, dextrin, pectin, low-substituted hydroxypropylcellulose, carboxymethylcellulose, carboxymethylcellulose calcium, croscarmellose sodium, carboxymethyl starch, and carboxymethyl starch sodium, and the like.

As coloring agents there may be mentioned those approved for addition to pharmaceuticals, such as iron sesquioxide, yellow iron sesquioxide, carmine, caramel, β-carotene, titanium oxide, talc, riboflavin sodium phosphate, yellow aluminum lake and the like.

As taste correctives there may be mentioned cocoa powder, menthol, aromatic powders, mentha oil, borneol, powdered cinnamon bark, and the like.

As emulsifiers or surfactants there may be mentioned stearyl triethanolamine, sodium lauryl sulfate, lauryl aminopropionic acid, lecithin, glycerin monostearate, sucrose fatty acid esters, glycerin fatty acid esters, and the like.

As dissolving aids there may be mentioned polyethylene glycol, propylene glycol, benzyl benzoate, ethanol, cholesterol, triethanolamine, sodium carbonate, sodium citrate, polysorbate 80, nicotinamide, and the like.

As suspending agents there may be mentioned the surfactants referred to above, as well as hydrophilic polymers such as polyvinyl alcohol, polyvinylpyrrolidone, methylcellulose, hydroxymethylcellulose, hydroxyethylcellulose, hydroxypropylcellulose and the like.

As isotonizing agents there may be mentioned glucose, sodium chloride, mannitol, sorbitol and the like.

As buffering agents there may be mentioned buffering solutions of phosphate, acetate, carbonate, citrate and the like.

As antiseptics there may be mentioned methylparaben, propylparaben, chlorobutanol, benzyl alcohol, phenethyl alcohol, dehydroacetic acid, sorbic acid, and the like.

As antioxidants there may be mentioned sulfite, ascorbic acid, α-tocopherol, and the like.

The formulation may be in the form of an oral preparation such as a tablet, powder, granule, capsule, syrup, lozenge or inhalant; an external preparation such as a suppository, ointment, eye salve, tape, eye drop, nasal drop, ear drop, pap or lotion; or an injection.

An oral preparation will be formulated using an appropriate combination of additives among those mentioned above. The surface thereof may also be coated if necessary.

An external preparation will be formulated using an appropriate combination of additives among those mentioned above, and particularly excipients, binders, taste correctives, emulsifiers, surfactants, dissolving aids, suspending agents, isotonizing agents, antiseptics, antioxidants, stabilizers and absorption accelerators.

An injection will be formulated using an appropriate combination of additives among those mentioned above, and particularly emulsifiers, surfactants, dissolving aids, suspending agents, isotonizing agents, buffering agents, antiseptics, antioxidants, stabilizers and absorption accelerators.

When the amorphous compound of the invention is to be used as a medicament, the dosage thereof will differ depending on the symptoms and age of the patient as well as the form of administration, but it will ordinarily be 100 μg to 10 g per day, administered at once or divided over several times.

The amorphous compound of the present invention is extremely useful as an angiogenesis inhibitor, and is also useful as a preventing or therapeutic agent for a disease for which angiogenesis inhibition is effective, an angiogenesis inhibitor, an anti-tumor agent, a therapeutic agent for angioma, a cancer metastasis inhibitor, a therapeutic agent for retinal neovascularization, a therapeutic agent for diabetic retinopathy, a therapeutic agent for an inflammatory disease, a therapeutic agent for an inflammatory disease selected from the group consisting of deformant arthritis, rheumatoid arthritis, psoriasis and delayed hypersensitivity reaction, and a therapeutic agent for atherosclerosis.

When using the amorphous compound of the present invention as an anti-tumor agent, examples of the tumor include a pancreatic cancer, a gastric cancer, a colon cancer, a breast cancer, a prostrate cancer, a lung cancer, a renal cancer, a brain tumor, a blood cancer or an ovarian cancer, and in particular, a gastric cancer, a colorectal cancer, a prostrate cancer, a lung cancer or a renal cancer are preferable.

Further, the amorphous compound of the present invention exhibits a strong inhibitory activity for c-Kit kinase, and is useful as an anti-cancer agent for a cancer which has undergone a malignant alteration due to activation of c-Kit kinase (for example, acute myelogenous leukemia, mast cell leukemia, a small cell lung cancer, GIST, a testicular tumor, an ovarian cancer, a breast cancer, a brain tumor, neuroblastoma or a colon cancer). The amorphous compound of the present invention is also useful as a therapeutic agent for a disease such as mastocytosis, allergy or asthma that is considered to be caused by c-Kit kinase.

EXAMPLE

Hereunder, examples are described to facilitate further understanding of the present invention, however, the following examples are not intended to limit the scope of the present invention.

Reference Example 1

Preparation of 4-(3-chloro-4-(cyclopropylaminocarbonyl)aminophenoxy)-7-methoxy-6-quinolinecarboxamide (1)

Phenyl N-(4-(6-carbamoyl-7-methoxy-4-quinolyl)oxy-2-chlorophenyl)carbamate (17.5 g, 37.7 mmol) disclosed in WO 02/32872 was dissolved in N,N-dimethylformamide (350 mL), and then cyclopropylamine (6.53 mL, 94.25 mmol) was added to the reaction mixture under a nitrogen atmosphere, followed by stirring overnight at room temperature. To the mixture was added water (1.75 L), followed by stirring. Precipitated crude crystals were collected by filtration, washed with water, and dried at 70° C. for 50 min. To the obtained crude crystals was added ethanol (300 mL), and then the mixture was heated under reflux for 30 min to dissolve, followed by stirring overnight to cool slowly down to room temperature. Precipitated crystals was collected by filtration and dried under vacuum, and then further dried at 70° C. for 8 hours to give the titled crystals (12.91 g, 80.2%).

Reference Example 2

Preparation of 4-(3-chloro-4-(cyclopropylaminocarbonyl)aminophenoxy)-7-methoxy-6-quinolinecarboxamide (2)

(1) Preparation of phenyl N-(2-chloro-4-hydroxyphenyl) carbamate

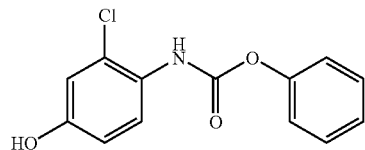

After suspending 4-amino-3-chlorophenol (23.7 g) in N,N-dimethylformamide (100 mL) and adding pyridine (23.4 mL) while cooling in on ice, phenyl chloroformate (23.2 mL) was added dropwise below 20° C. Stirring was performed at room temperature for 30 min, and then water (400 mL), ethyl acetate (300 mL) and 6N-HCl (48 mL) were added, the mixture was stirred, and the organic layer was separated. The organic layer was washed twice with a 10% aqueous solution of sodium chloride (200 mL), and dried over magnesium sulfate. The solvent was removed to give 46 g of the titled compound as a solid.

$^1$H-NMR Spectrum (CDCl$_3$) δ(ppm): 5.12 (1H, br s), 6.75 (1H, dd, J=9.2, 2.8 Hz), 6.92 (1H, d, J=2.8 Hz), 7.18-7.28 (4H, m), 7.37-7.43 (2H, m), 7.94 (1H, br s).

(2) Preparation of 1-(2-chloro-4-hydroxyphenyl)-3-cyclopropylurea

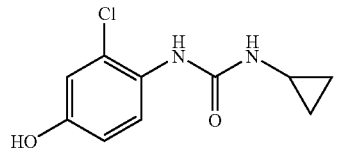

After dissolving phenyl N-(2-chloro-4-hydroxyphenyl) carbamate in N,N-dimethylformamide (100 mL), cyclopropylamine (22.7 mL) was added while cooling on ice, and the mixture was stirring at room temperature overnight. Water (400 mL), ethyl acetate (300 mL) and 6N-HCl (55 mL) were then added, the mixture was stirred, and the organic layer was separated. The organic layer was washed twice with a 10% aqueous solution of sodium chloride (200 mL), and dried over magnesium sulfate. Prism crystals obtained by concentrating the solvent were filtered and washed with heptane to give 22.8 g of the titled compound (77% yield from 4-amino-3-chlorophenol).

$^1$H-NMR Spectrum (CDCl$_3$) δ(ppm): 0.72-0.77 (2H, m), 0.87-0.95 (2H, m), 2.60-2.65 (1H, m), 4.89 (1H, br s), 5.60 (1H, br s), 6.71 (1H, dd, J=8.8, 2.8 Hz), 6.88 (1H, d, J=2.8 Hz), 7.24-7.30 (1H, br s), 7.90 (1H, d, J=8.8 Hz)

(3) Preparation of 4-(3-chloro-4-(cyclopropylaminocarbonyl)aminophenoxy)-7-methoxy-6-quinolinecarboxamide To dimethylsulfoxide (20 mL) were added 7-methoxy-4-chloroquinoline-6-carboxamide (0.983 g), 1-(2-chloro-4-hydroxyphenyl)-3-cyclopropylurea (1.13 g) and cesium carbonate (2.71 g), followed by heating and stirring at 70° C. for 23 hours. After the reaction mixture was allowed to cool down to room temperature, water (50 mL) was added, and the produced crystals were collected by filtration to give 1.56 g of the titled compound (88% yield).

Reference Example 3

Preparation of 4-(3-chloro-4-(cyclopropylaminocarbonyl)aminophenoxy)-7-methoxy-6-quinolinecarboxamide (3)

In a reaction vessel were placed 7-methoxy-4-chloroquinoline-6-carboxamide (5.00 kg, 21.13 mol), dimethylsulfoxide (55.05 kg), 1-(2-chloro-4-hydroxyphenyl)-3-cyclopropylurea (5.75 kg, 25.35 mol) and potassium t-butoxide (2.85 kg, 25.35 mol) in that order, under a nitrogen atmosphere. After stirring at 20° C. for 30 min, the temperature was raised to 65° C. over a period of 2.5 hours. After stirring at the same temperature for 19 hours, 33% (v/v) acetone water (5.0 L) and water (10.0 L) were added dropwise over a period of 3.5 hours. Upon completion of the dropwise addition, the mixture was stirred at 60° C. for 2 hours, and 33% (v/v) acetone water (20.0 L) and water (40.0 L) were added dropwise at 55° C. or higher over a period of 1 hour. After then stirring at 40° C. for 16 hours, the precipitated crystals were collected by filtration using a nitrogen pressure filter, and the crystals were washed with 33% (v/v) acetone water (33.3 L), water (66.7 L), and acetone (50.0 L) in that order. The obtained crystals were dried at 60° C. for 22 hours using a conical vacuum dryer to give 7.78 kg of the titled compound (96.3% yield).

$^1$H-NMR chemical shift values for 4-(3-chloro-4-(cyclopropylaminocarbonyl)aminophenoxy)-7-methoxy-6-quinolinecarboxamides obtained in Reference Examples 1 to 3 above corresponded to those for 4-(3-chloro-4-(cyclopropylaminocarbonyl)aminophenoxy)-7-methoxy-6-quinolinecarboxamide disclosed in WO 02/32872.

Reference Example 4

A crystalline form of the hydrochloride of 4-(3-chloro-4-(cyclopropylaminocarbonyl)aminophenoxy)-7-methoxy-6-quinolinecarboxamide After suspending and stirring 4-(3-chloro-4-(cyclopropylaminocarbonyl)aminophenoxy)-7-methoxy-6-quinolinecarboxamide (854 mg, 2.0 mmol) in ethanol (17 mL), 2N hydrochloric acid (1.1 mL, 2.2 mmol) was added dropwise to the reaction mixture while refluxing using an oil bath with an external temperature of 100° C. After confirming that the suspension had changed into a solution, the heating of the oil bath was stopped, and the mixture was allowed to slowly cool down to room temperature while immersed in the oil bath, followed by stirring overnight. Ethanol (8.6 mL) was added to the reaction mixture, and the crystals were collected by filtration, washed with ethanol (4.3 mL×2), dried under aeration on filter paper (1.5 hours), and then dried (23 hours) with hot air at 70° C. to give the titled crystals (786.1 mg, 85%).
$^1$H-NMR Spectrum (DMSO-$d_6$) δ(ppm): 0.30-0.50 (2H, m), 0.60-0.70 (2H, m), 2.56 (1H, m), 4.06 (3H, s), 6.86 (1H, d, J=6.4 Hz), 7.29-7.35 (2H, m), 7.60 (1H, d, J=2.8 Hz), 7.64 (1H, s), 7.88 (1H, s), 7.95 (1H, s), 8.07 (1H, s), 8.34 (1H, d, J=9.2 Hz), 8.70 (1H, s), 8.91 (1H, d, J=6.4 Hz).

Reference Example 5

A crystalline form of the hydrobromide of 4-(3-chloro-4-(cyclopropylaminocarbonyl)aminophenoxy)-7-methoxy-6-quinolinecarboxamide After suspending and stirring 4-(3-chloro-4-(cyclopropylaminocarbonyl)aminophenoxy)-7-methoxy-6-quinolinecarboxamide (500 mg, 1.17 mmol) in ethanol (10 mL), an aqueous solution of 1N hydrobromic acid (1.3 mL, 1.3 mmol) was then added dropwise to the reaction mixture while refluxing using an oil bath with an external temperature of 100° C. After water (2.0 mL) was gradually added to the mixture to form a solution, the heating of the oil bath was stopped, and the mixture was allowed to slowly cool down to room temperature while immersed in the oil bath, followed by stirring overnight. Precipitated crystals were collected by filtration, washed with ethanol (2.5 mL×2), dried under aeration on filter paper (15 min), and then dried (22 hours) with hot air at 100° C. to give the titled crystals (483.7 mg, 81%).
$^1$H-NMR Spectrum (DMSO-$d_6$) δ(ppm): 0.40-0.50 (2H, m), 0.60-0.70 (2H, m), 2.58 (1H, m), 4.09 (3H, s), 6.89 (1H, d, J=6.4 Hz), 7.26 (1H, d, J=2.8 Hz), 7.33 (1H, dd, J=2.8, 9.2 Hz), 7.59 (1H, s), 7.62 (1H, d, J=2.8 Hz), 7.90 (1H, s), 7.96 (1H, s), 8.06 (1H, s), 8.36 (1H, d, J=9.2 Hz), 8.72 (1H, s), 8.93 (1H, d, J=6.4 Hz).

Reference Example 6

A crystalline form of the p-toluenesulfonate of 4-(3-chloro-4-(cyclopropylaminocarbonyl)aminophenoxy)-7-methoxy-6-quinolinecarboxamide Dimethylsulfoxide (1.5 mL) and p-toluenesulfonic acid monohydrate (80 mg, 0.422 mmol) were added to 4-(3-chloro-4-(cyclopropylaminocarbonyl)aminophenoxy)-7-methoxy-6-quinolinecarboxamide (150 mg, 0.351 mmol) at room temperature. Although a solution was temporarily formed, crystals precipitated immediately. Therefore, dimethylsulfoxide (2.25 mL) was added to the reaction mixture at 80° C. to dissolve the crystals. The mixture was allowed to slowly cool down to room temperature, and stirred for 14 hours. Precipitated crystals were collected by filtration and dried at 60° C. to give the titled crystals (177 mg).
$^1$H-NMR Spectrum (400 MHz, DMSO-$d_6$) δ(ppm): 0.39 (2H, m), 0.63 (2H, m), 2.24 (3H, s), 2.54 (1H, m), 4.04 (3H, s), 6.88 (1H, d, J=6.4 Hz), 7.05 (1H, s), 7.07 (1H, s), 7.21 (1H, d, J=2.8 Hz), 7.31 (1H, dd, J=2.6, 9.3 Hz), 7.41 (1H, s), 7.43 (1H, s), 7.59 (1H, d, J=2.8 Hz), 7.86 (1H, s), 7.92 (1H, s), 8.02 (1H, s), 8.32 (1H, d, J=9.6 Hz), 8.68 (1H, s), 8.91 (1H, d, J=6.4 Hz)

Reference Example 7

A crystalline form of the sulfate of 4-(3-chloro-4-(cyclopropylaminocarbonyl)aminophenoxy)-7-methoxy-6-quinolinecarboxamide Dimethylsulfoxide (1.5 mL) and sulfuric acid (23 μL, 0.422 mmol) were added to 4-(3-chloro-4-cyclopropylaminocarbonyl)aminophenoxy)-7-methoxy-6-quinolinecarboxamide (150 mg, 0.351 mmol) at room temperature. Although a solution was temporarily formed, crystals precipitated immediately. Therefore, dimethylsulfoxide (2.25 mL) was added to the reaction mixture at 80° C. to dissolve the crystals. The mixture was allowed to slowly cool down to room temperature, and stirred for 16 hours. Precipitated crystals were collected by filtration and dried at 60° C. to give the titled crystals (174 mg).
$^1$H-NMR Spectrum (400 MHz, DMSO-$d_6$) δ(ppm): 0.39 (2H, m), 0.63 (2H, m), 2.46 (2H, d, J=1.2 Hz), 2.52 (1H, m), 4.04 (3H, s), 6.88 (1H, d, J=5.8 Hz), 7.21 (1H, s), 7.31 (1H, d, J=8.2 Hz), 7.56 (1H, s), 7.59 (1H, s), 7.86 (1H, s), 7.93 (1H, s), 8.02 (1H, s), 8.33 (1H, d, J=8.2 Hz), 8.68 (1H, s), 8.91 (1H, d, J=5.8 Hz)

Reference Example 8

A crystalline form of the methanesulfonate of 4-(3-chloro-4-(cyclopropylaminocarbonyl)aminophenoxy)-7-methoxy-6-quinolinecarboxamide (Form A)

(Preparation Method 1)
In a mixed solution of methanol (14 mL) and methanesulfonic acid (143 μL, 1.97 mmol) was dissolved 4-(3-chloro-4-(cyclopropylaminocarbonyl)aminophenoxy)-7-methoxy-6-quinolinecarboxamide (700 mg, 1.64 mmol) at 70° C. After confirming the dissolution of 4-(3-chloro-4-(cyclopropylaminocarbonyl)aminophenoxy)-7-methoxy-6-quinolinecarboxamide, the reaction mixture was allowed to cool down to room temperature over a period of 5.5 hours, further stirred at room temperature for 18.5 hours, and crystals were collected by filtration. The resultant crystals were dried at 60° C. to give the titled crystals (647 mg).

(Preparation Method 2)
In a mixed solution of acetic acid (6 mL) and methanesulfonic acid (200 μL, 3.08 mmol) was dissolved 4-(3-chloro-4-(cyclopropylaminocarbonyl)aminophenoxy)-7-methoxy-6-quinolinecarboxamide (600 mg, 1.41 mmol) at 50° C. After confirming the dissolution of 4-(3-chloro-4-(cyclopropylaminocarbonyl)aminophenoxy)-7-methoxy-6-quinolinecarboxamide, ethanol (7.2 mL) and seed crystals of a crystalline form of the methanesulfonate of 4-(3-chloro-4-(cyclopropylaminocarbonyl)aminophenoxy)-7-methoxy-6-quinolinecarboxamide (Form A) (12 mg) were added in that order to the reaction mixture, and ethanol (4.8 mL) was further added dropwise over a period of 2 hours. Upon completion of the dropwise addition, the reaction mixture was stirred at 40° C. for 1 hour then at room temperature for 9 hours, and crystals were collected by filtration. The resultant crystals were dried at 60° C. to give the titled crystals (545 mg).

Reference Example 9

A crystalline form of the methanesulfonate of 4-(3-chloro-4-(cyclopropylaminocarbonyl)aminophenoxy)-7-methoxy-6-quinolinecarboxamide (Form B)

A crystalline form of the acetic acid solvate of the methanesulfonate of 4-(3-chloro-4-(cyclopropylaminocarbonyl) aminophenoxy)-7-methoxy-6-quinolinecarboxamide (Form I) (250 mg) obtained in Reference Example 13 was dried under aeration at 30° C. for 3 hours and at 40° C. for 16 hours to give the titled crystals (240 mg).

Reference Example 10

A crystalline form of the methanesulfonate of 4-(3-chloro-4-(cyclopropylaminocarbonyl)aminophenoxy)-7-methoxy-6-quinolinecarboxamide (Form C)

(Preparation method 1)
n-Butyl acetate (12 mL) was added to a crystalline form of the dimethylsulfoxide solvate of the methanesulfonate of 4-(3-chloro-4-(cyclopropylaminocarbonyl)aminophenoxy)-7-methoxy-6-quinolinecarboxamide (600 mg, 1.15 mmol) obtained in Reference Example 11 (Preparation method 1), and the reaction mixture was stirred at 115° C. for 10 hours and further stirred at room temperature for 1.5 hours. The resultant crystals were then collected by filtration and dried at 60° C. to give the titled crystals (503 mg).

(Preparation method 2)
Ethanol (6.4 mL) was added to a crystalline form of the acetic acid solvate of the methanesulfonate of 4-(3-chloro-4-(cyclopropylaminocarbonyl)aminophenoxy)-7-methoxy-6-quinolinecarboxamide (Form I) (1.28 g) obtained in Reference Example 13, followed by dissolution at 40° C., and then the reaction mixture was stirred at the same temperature for 36 hours. Precipitated crystals were collected by filtration and dried at 50° C. to give the titled crystals (0.87 g).

(Preparation method 3)
To a mixed solution of acetic acid (14 mL) and methanesulfonic acid (0.37 mL, 5.62 mmol), 4-(3-chloro-4-(cyclopropylaminocarbonyl)aminophenoxy)-7-methoxy-6-quinolinecarboxamide (2.00 g, 4.69 mmol) was added, followed by dissolution at 40° C. After confirming the dissolution, 2-propanol (9 mL) and seed crystals of a crystalline form of the methanesulfonate of 4-(3-chloro-4-(cyclopropylaminocarbonyl)aminophenoxy)-7-methoxy-6-quinolinecarboxamide (Form C) (100 mg) were added in that order to the reaction mixture, and the reaction mixture was stirred for 20 min. Isopropyl acetate (10 mL) was then further added dropwise over 30 min. Upon completion of the dropwise addition of isopropyl acetate, the reaction mixture was stirred for 1.5 hours, and further stirred at 15° C. for 14 hours. Precipitated crystals were collected by filtration and dried at 60° C. to give the titled crystals (2.22 g).

(Preparation method 4)
4-(3-Chloro-4-(cyclopropylaminocarbonyl)aminophenoxy)-7-methoxy-6-quinolinecarboxamide (1.28 g, 3 mmol) was mixed with acetic acid (12.8 ml), and to this suspension was added methanesulfonic acid (0.408 ml, 6.3 mmol), followed by stirring at room temperature to dissolve. The reaction mixture was heated with a bath at a temperature of 30° C., and 2-propanol (7.7 ml) was added. Seed crystals of a crystalline form of the methanesulfonate of 4-(3-chloro-4-(cyclopropylaminocarbonyl)aminophenoxy)7-methoxy-6-quinolinecarboxamide (Form C) was added, and 2-propanol was further added 14 times by every amount of 1.28 ml over a period of 44 min. The warm bath was removed, the reaction mixture was stirred for 10 min at room temperature, then for 5 min in a water bath, and for 25 min in a water bath with a small amount of ice (internal temperature: 17.6° C). Resultant crystals were collected by filtration and washed with 2-propanol (10 ml). The crystals obtained after the filtration were stirred in ethanol (6.4 ml) at room temperature for 1 hour. The resultant crystals were collected by filtration, washed with ethanol (4 ml) and dried at 60° C. to give the titled crystals (1068 mg).

Reference Example 11

A Crystalline form of the dimethylsulfoxide solvate of methanesulfonate of 4(3-chloro-4(cyclopropylaminocarbonyl)aminophenoxy) -7-methoxy-6-quinolinecarboxamide (Preparation method 1)
To 4-3-chloro-4-(cyclopropylaminocarbonyl)aminophenoxy)-7-methoxy -6-quinolinecarboxamide (700 mg, 1.640 mmol) was added dimethylsulfoxide (7 mL) at room temperature, followed by dissolution at 80° C. Methanesulfonic acid (143 µL, 1.97 mmol), ethyl acetate (1.4 mL) and seed crystals of a crystalline form of the methanesulfonate of 4-(3-chloro-4-(cyclopropylaminocarbonyl)aminophenoxy)-7-methoxy-6-quinolinecarboxamide (Form A) were added in that order to the reaction mixture at 60° C., and ethyl acetate (5.6 mL) was further added dropwise over a period of 45 min. 15 min after completion of the dropwise addition of ethyl acetate, the reaction mixture was allowed to cool down to room temperature over a period of 1 hour, followed by stirring at the same temperature for 18 hours. Precipitated crystals were collected by filtration and dried at 60° C. to give the titled crystals (746 mg).

(Preparation method 2)
To 4-(3-chloro-4-(cyclopropylaminocarbonyl)aminophenoxy)-7-methoxy -6-quinolinecarboxamide (854 mg, 2 mmol) was added dimethylsulfoxide (6.8 mL) at room temperature, followed by dissolution at 60° C. Methanesulfonic acid (389 µL, 6 mmol) and seed crystals of a crystalline form of the methanesulfonate of 4-(3-chloro-4cyclopropylaminocarbonyl)aminophenoxy)-7-methoxy-6-quinolinecarboxamide (Form A) were added in that order to the reaction mixture at the same temperature, and 2-propanol (6.8 mL) was then added dropwise over a period of 30 min. After completion of the dropwise addition of 2-propanol, the reaction mixture was cooled to 15° C. over a period of 2 hours, followed by stirring at the same temperature for 30 min. Precipitated crystals were collected by filtration and dried at 60° C. to give the titled crystals (1095 mg).

(Preparation method 3)
To 4-chloro-4-cyclopropylaminocarbonyl)aminophenoxy)-7-methoxy -6-quinolinecarboxamide (854 mg, 2 mmol) was added dimethylsulfoxide (6.8 mL) at room temperature, followed by dissolution at 62° C. Methanesulfonic acid (454 µL, 7 mmol) and seed crystals of a crystalline form of the methanesulfonate of 4-(3-chloro-4-(cyclopropylaminocarbonyl)aminophenoxy)-7-methoxy-6-quinolinecarboxamide (Form A) were added in that order to the reaction mixture at the same temperature, and 2-propanol (13.6 mL) was then added dropwise over a period of 1 hour. After completion of the dropwise addition of 2-propanol, the reaction mixture was cooled to 15° C. over a period of 2 hours, followed by stirring at the same temperature for 30 min. Precipitated crystals were collected by filtration and dried at 60° C. to give the titled crystal (1082 mg).

Reference Example 12

A crystalline form of the hydrate of the methanesulfonate of 4-(3-chloro-4-(cyclopropylaminocarbonyl)aminophenoxy)-7-methoxy-6-quinolinecarboxamide (Form F)

In a mixed solution of acetic acid (1.5 mL) and methanesulfonic acid (31 µL, 0.422 mmol) was dissolved 4-(3-chloro-4-(cyclopropylaminocarbonyl)aminophenoxy)-7-methoxy-6-quinolinecarboxamide (150 mg, 0.351 mmol) at 50° C. After confirming the dissolution, ethyl acetate (0.6 mL) and a crystalline form of the methanesulfonate of 4-(3-chloro-4-(cyclopropylaminocarbonyl)aminophenoxy)-7-methoxy-6-quinolinecarboxamide (Form A) obtained in Reference Example 8 (Preparation method 1) were added in that order to the reaction mixture, and ethyl acetate (1.8 mL) was further added dropwise over a period of 2 hours. Upon completion of the dropwise addition of ethyl acetate, the reaction mixture was stirred at 50° C. for 30 min, and then stirred at room temperature for 7.5 hours. Precipitated crystals were collected by filtration and dried at 60° C. to give the titled crystals (176 mg).

Reference Example 13

A crystalline form of the acetic acid solvate of the methanesulfonate of 4-(3-chloro-4-(cyclopropylaminocarbonyl) aminophenoxy)-7-methoxy-6quinolinecarboxamide (Form I)

In a mixed solution of acetic acid (14 mL) and methanesulfonic acid (0.36 mL, 5.62 mmol) was dissolved 4-(3-chloro-4-(cyclopropylaminocarbonyl)aminophenoxy)-7-methoxy-6-quinolinecarboxamide (2.00 g, 4.69 mmol) at 40° C. After confirming the dissolution, 1-propanol (4 mL) and seed crystals of a crystalline form of the methanesulfonate of 4-(3-chloro -4-(cyclopropylaminocarbonyl)aminophenoxy)-7-methoxy-6-quinolinecarboxamide (Form C) (100 mg) were added in that order to the reaction mixture, and 1-propanol (14 mL) and isopropyl acetate (10 mL) were further added dropwise over a period, of 1 hour. Upon completion of the dropwise addition, the reaction mixture was stirred at 40° C. for 1 hour, and then stirred at 25° C. for a further 40 min. Precipitated crystals were collected by filtration to give the titled crystals (2.61 g).

The $^1$H-NMR chemical shift values for the methanesulfonate are as follows:

$^1$H-NMR Spectrum (DMSO-$d_6$) δ(ppm): 0.44 (2H, m), 0.67 (2H, m), 2.36 (3H, s), 2.59 (1H, m), 4.09 (3H, s), 6.95 (1H, d, J=7 Hz), 7.25 (1H, d, J=2 Hz), 7.36 (1H, dd, J=3, 9 Hz), 7.63 (1H, d, J=3 Hz), 7.65 (1H, s), 7.88 (1H, brs), 7.95 (1H, brs), 8.06 (1H, s), 8.37 (1H, d, J=9 Hz), 8.73 (1H, s), 8.97 (1H, d, J=7 Hz)

Reference Example 14

A crystalline form of the ethanesulfonate of 4-(3-chloro-4-(cyclopropylaminocarbonyl)aminophenoxy)-7-methoxy-6-quinolinecarboxamide (Form α)

(Preparation method 1)
To 4-(3-chloro-4-(cyclopropylaminocarbonyl)aminophenoxy)-7-methoxy -6-quinolinecarboxamide (150 mg, 0.351 mmol) were added dimethylsulfoxide (1.5 mL) and ethanesulfonic acid (34 µL, 0.422 mmol) at room temperature for dissolution. Ethyl acetate (1.5 mL) was added dropwise to the reaction mixture at 60° C. over a period of 1.5 hours. 30 min after completion of the dropwise addition of ethyl acetate, the reaction mixture was allowed to cool down to room temperature over a period of 1.5 hours, followed by further stirring at room temperature for 7 hours. Precipitated crystals were collected by filtration and dried at 60° C. to give the titled crystals (176 mg).

(Preparation method 2)
To 4-(3-chloro-4-(cyclopropylaminocarbonyl)aminophenoxy)-7-methoxy -6-quinolinecarboxamide (150 mg, 0.351 mmol) were added ethanol (40 mL) and ethanesulfonic acid (459 µL, 5.622 mmol) at room temperature, followed by dissolution at 65° C. The reaction mixture was cooled with a bath at a temperature of 22° C., and seed crystals of a crystalline form of the ethanesulfonate of 4-(3-chloro-4-(cyclopropylaminocarbonyl)aminophenoxy)-7-methoxy-6-quinolinecarboxamide (Form α) was added. The mixture was further stirred for 7 hours. Precipitated crystals were collected by filtration and dried at 70° C. to give the titled crystals (1.55 g).

Reference Example 15

A crystalline form of the ethanesulfonate of 4-(3-chloro4-(cyclopropylaminocarbonyl)aminophenoxy)-7-methoxy-6-quinolinecarboxamide (Form β)

(Preparation method 1)
To a crystalline form of the ethanesulfonate of 4-(3-chloro-4-(cyclopropylaminocarbonyl)aminophenoxy)-7-methoxy-6-quinolinecarboxamide (Form α) (198 mg) obtained in Example 11 were added ethanol (3 mL) and water (0.5 mL), and the reaction mixture was stirred at room temperature for 3 hours. Crystals were collected by filtration and dried at 60° C. to give the titled crystals (89 mg).

(Preparation method 2)
To 4-(3-chloro-4-(cyclopropylaminocarbonyl)aminophenoxy)-7-methoxy -6-quinolinecarboxamide (150 mg, 0.351 mmol) were added acetic acid (0.75 mL) and ethanesulfonic acid (34 µL, 0.422 mmol) at room temperature, followed by dissolution at 60° C. To the reaction mixture were added water (0.225 mL), 2-propanol (2 mL), a crystalline form of the ethanesulfonate of 4-(3-chloro-4-(cyclopropylaminocarbonyl)aminophenoxy)-7-methoxy-6-quinolinecarboxamide (Form β) obtained in Reference Example 15 (Preparation method 1), and 2-propanol (2.5 mL) in that order, and the mixture was then cooled to 0° C. over a period of 2.5 hours, and stirred for 30 min. Precipitated crystals were collected by filtration and dried at 60° C. to give the titled crystals (139 mg).

Reference Example 16

A crystalline form of the dimethylsulfoxide solvate of the ethanesulfonate of 4-(3-chloro-4-(cyclopropylaminocarbonyl)aminophenoxy)-7-methoxy-6-quinolinecarboxamide To 4-3-chloro-4-(cyclopropylaminocarbonyl)aminophenoxy)-7-methoxy -6-quinolinecarboxamide (400 mg, 0.937 mmol) was added dimethylsulfoxide (4 mL) at room temperature, followed by dissolution at 60° C. To the reaction mixture were added ethanesulfonic acid (92 µL, 1.124 mmol), ethyl acetate (2.4 mL) and a crystalline form of the ethanesulfonate of 4-(3-chloro-4-(cyclopropylaminocarbonyl)aminophenoxy)-7-methoxy-6-quinolinecarboxamide (Form β) obtained in Reference Example 15 (Preparation method 1) in that order, and the mixture was then stirred at 60° C. for 20 min. After a further addition of ethyl acetate (1.6 mL), the reaction mixture was once heated to 80° C., and then cooled to 0° C. over a period of 1.5 hours. Precipitated crystals were collected by filtration and dried at 60° C. to give the titled crystals (523 mg).

The $^1$H-NMR chemical shift values for the ethanesulfonate are as follows:

$^1$H-NMR Spectrum (DMSO-d$_6$) δ(ppm): 0.43 (2H, m), 0.66 (2H, m), 1.05 (3H, t, J=7.4 Hz), 2.38 (2H, q, J=7.4 Hz), 2.58 (1H, m), 4.08 (3H, s), 6.88 (1H, s), 7.24 (1H, s), 7.34 (1H, d, J=9.0 Hz), 7.60 (1H, s), 7.61 (1H, s), 7.88 (1H, s), 7.94 (1H, s), 8.05 (1H, s), 8.36 (1H, d, J=9.0 Hz), 8.72 (1H, s), 8.92 (1H, s)

Example 1

An amorphous form of the methanesulfonate of 4-(3-chloro-4-(cyclopropylaminocarbonyl)aminophenoxy)-7-methoxy-6-quinolinecarboxamide

To a crystalline form of the methanesulfonate of 4-(3-chloro-4-(cyclopropylaminocarbonyl)aminophenoxy)-7-methoxy-6-quinolinecarboxamide (Form C) obtained in Reference Example 10 (Preparation method 3) (200 mg, 0.382 mmol) was added ethanol (8 mL) at room temperature. Water (8 mL) was added at room temperature for dissolution. The solution was filtered, and the filtrate was concentrated under reduced pressure to remove ethanol. The solution was frozen in a dry ice ethanol bath, lyophilized for about 3 days to give the titled amorphous compound (169 mg, pale yellow).

Example 2

An amorphous form of the ethanesulfonate of 4-(3-chloro-4-(cyclopropylaminocarbonyl)aminophenoxy)-7-methoxy-6-quinolinecarboxamide

To a crystalline form of the ethanesulfonate of 4-(3-chloro-4-(cyclopropylaminocarbonyl)aminophenoxy)-7-methoxy-6-quinolinecarboxamide (Form α) obtained in the Reference Example 14 (Preparation method 2) (200 mg, 0.372 mmol) was added ethanol (8 mL) at room temperature. Water (8 mL) was added at room temperature for dissolution. The solution was filtered, and the filtrate was concentrated under reduced pressure to remove ethanol. The solution was frozen in a dry ice ethanol bath, lyophilized for about 5 days to give the titled amorphous compound (178 mg, pale yellow).

(Powder X-ray Diffraction Measurement)

Powder X-ray diffraction analysis was carried out for crystals obtained in Reference Examples 1, 4, 5, 6, 7, 8, 9 10, 12, 13, 14 and 15 and amorphous compounds obtained in Examples 1 and 2 under the following measurement conditions in accordance with "X-Ray Powder Diffraction Method" described in Japanese Pharmacopoeia 14th Edition, General Tests (B-614 to 619).

Apparatus: RINT-2000 (manufactured by Rigaku Denki KK)

X-ray: CuKα ray

Monochrometer: curved crystal monochrometer

Goniometer: vertical goniometer

Counter: scintillation counter

Applied voltage: 40 kV

Charging current: 200 mA

Scan speed: 5°/min (2°/min with respect to a crystalline form of the free form of the carboxamide obtained in Reference Example 1, a crystalline form of the hydrochloride obtained in Reference Example 4, a crystalline form of the hydrobromide obtained in Reference Example 5, a crystalline form of the acetic acid solvate of the mesylate (Form I) obtained in Reference Example 13, an amorphous form of the mesylate obtained in Example 1 and an amorphous form of the ethanesulfonate obtained in Example 2)

Scan axis: 2θ/θ

Scan range: 2θ=5 to 40°

Divergent slit: 0.5°

Scattering slit: 0.5°

Receiving slit: 0.3 mm

The powder X-ray diffraction patterns for crystals obtained in Reference Examples 1, 4, 5, 6, 7, 8, 9 10, 12, 13, 14 and 15 and amorphous compounds obtained in Examples 1 and 2 are shown in FIGS. 1 to 14, respectively.

(Infrared Absorption Spectrum Measurement)

Infrared absorption spectrum measurement was carried out for amorphous compounds obtained in Examples 1 and 2 according to the ATR method in the infrared absorption spectrum method as described in the Japanese Pharmacopoeia 14th Edition, General Tests by using FT-IR Spectrum-One (manufactured by PerkinElmer Japan Co., Ltd.) with a measurement range of 4000-400 cm$^{-1}$ and a resolution of 4 cm$^{-1}$.

Figure 15:
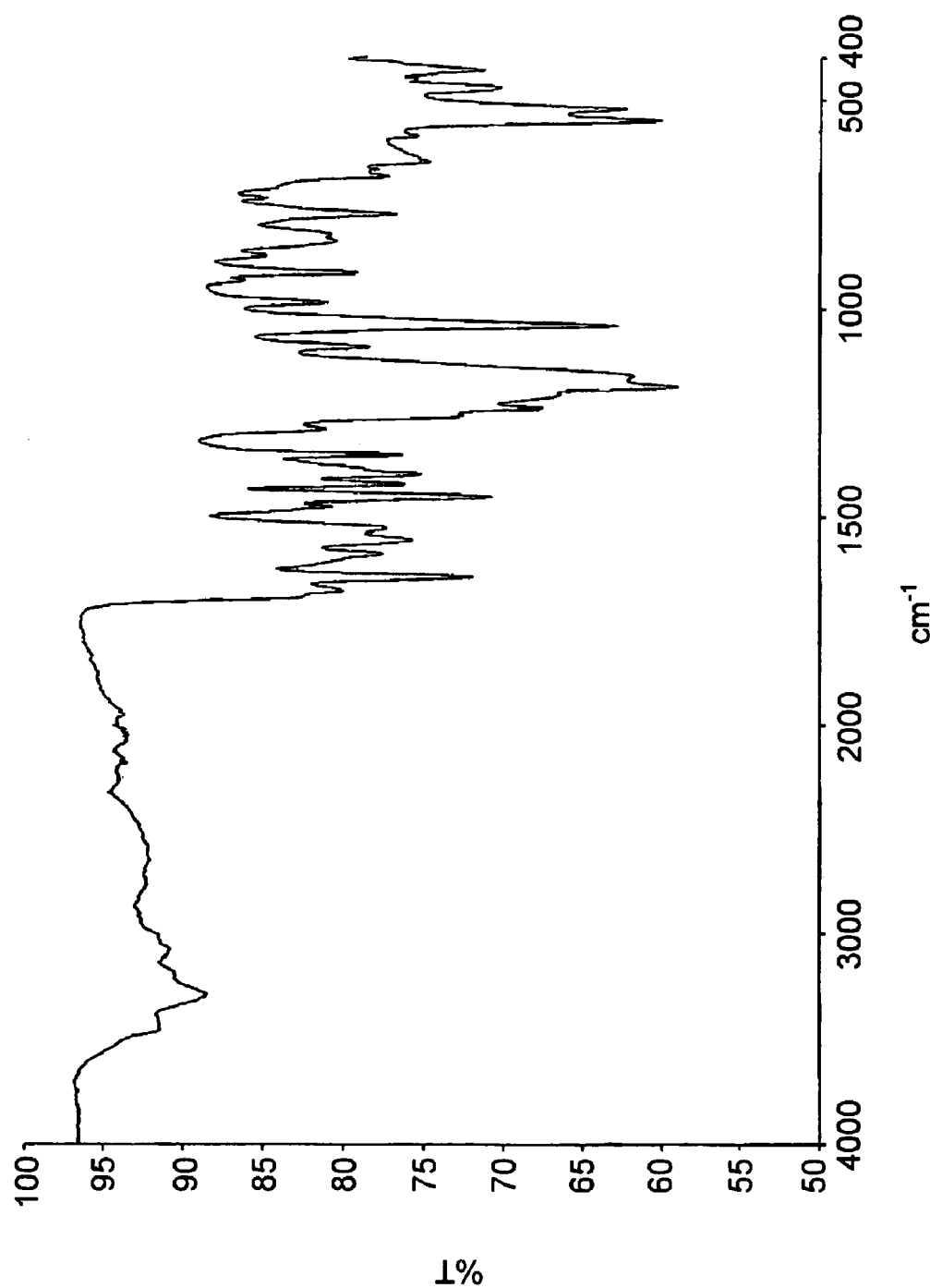
FIG. 15 is a figure illustrating an infrared absorption spectrum for an amorphous form of the methanesulfonate of the carboxamide obtained in Example 1.
Figure 16:
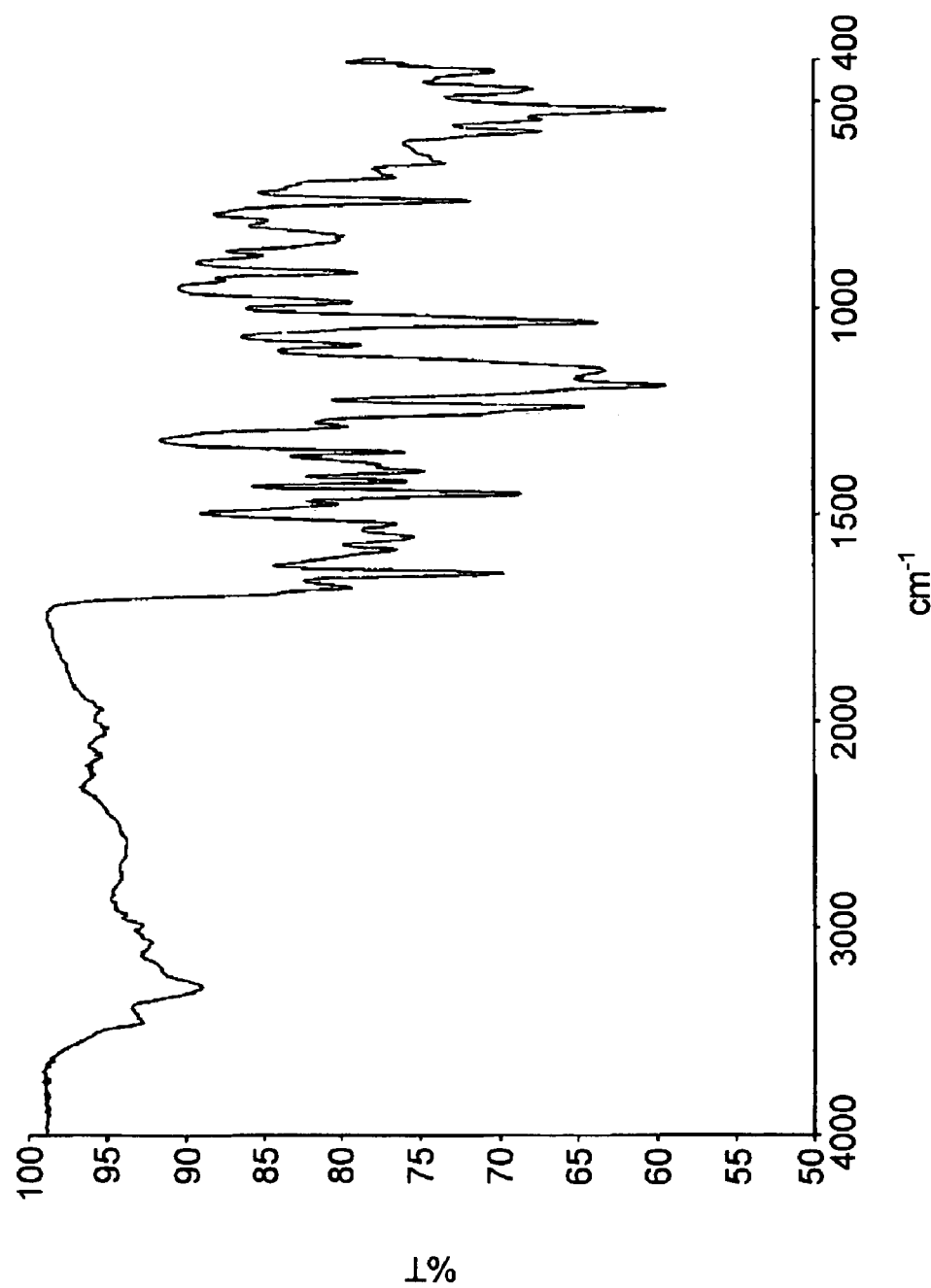
FIG. 16 is a figure illustrating an infrared absorption spectrum for an amorphous form of the ethanesulfonate of the carboxamide obtained in Example 2.

The infrared absorption spectra of the amorphous compounds obtained in Examples 1 and 2 are shown in FIGS. 15 and 16, respectively, and wave numbers of the absorption peaks (cm$^{-1}$) and transmittance (%T) are listed in Tables 1 and 2, respectively.

TABLE 1

| amorphous mesylate | |
|---|---|
| wavenumber (cm$^{-1}$) | % T |
| 3287.22 | 88.49 |
| 2050.36 | 96.36 |
| 1677.83 | 79.99 |
| 1644.37 | 71.87 |
| 1588.94 | 77.61 |
| 1556.13 | 75.74 |
| 1527.04 | 77.35 |
| 1476.47 | 80.71 |
| 1452.71 | 70.76 |
| 1421.59 | 76.16 |
| 1398.51 | 75.15 |
| 1351.71 | 76.35 |
| 1290.17 | 81.05 |
| 1238.35 | 67.53 |
| 1187.28 | 58.94 |
| 1091.53 | 78.33 |
| 1039.95 | 62.79 |
| 985.58 | 80.93 |
| 914.48 | 79.10 |
| 874.25 | 84.76 |
| 839.02 | 80.44 |
| 774.87 | 76.69 |
| 737.57 | 84.73 |
| 684.90 | 77.20 |
| 649.89 | 74.64 |
| 551.00 | 60.02 |
| 522.82 | 62.20 |
| 471.97 | 70.15 |
| 430.97 | 71.16 |

TABLE 2 amorphous ethanesulfonate

| wavenumber (cm$^{-1}$) | % T |
|---|---|
| 3287.26 | 88.92 |
| 2582.80 | 93.63 |
| 2034.67 | 94.85 |
| 1679.03 | 79.21 |
| 1644.66 | 69.70 |
| 1587.37 | 76.35 |
| 1557.46 | 75.32 |
| 1524.53 | 76.38 |
| 1476.68 | 80.10 |
| 1451.51 | 68.55 |
| 1421.62 | 75.75 |
| 1397.89 | 74.59 |
| 1351.00 | 75.87 |
| 1289.75 | 79.48 |
| 1239.49 | 64.52 |
| 1187.79 | 59.39 |
| 1151.46 | 63.23 |
| 1090.63 | 78.63 |
| 1035.17 | 63.67 |
| 985.37 | 79.18 |
| 914.27 | 78.83 |
| 873.30 | 84.95 |
| 826.16 | 79.72 |
| 788.40 | 84.67 |
| 741.72 | 71.77 |
| 683.83 | 76.42 |
| 650.40 | 73.31 |
| 574.21 | 67.31 |
| 519.67 | 59.34 |
| 471.19 | 67.80 |
| 427.43 | 70.25 |

Test Example 1

Test for Measuring Dissolution Rate

[Method]

The dissolution rates of the following crystal and amorphous compounds were measured under the conditions described below by the rotating disk method (see, J. H. Woods et al., J. Pharm. Soc., 54, 1068 (1955)): a crystalline form of the free carboxamide obtained in Preparation Example 1, an amorphous form of the methanesulfonate of the carboxamide obtained in Example 1 and an amorphous form of the ethanesulfonate obtained in Example 2. The dissolution rates were calculated based on a range in which linearity was maintained in the relation between concentration and time at the initial stage of dissolution.

(Rotating disk method conditions)

Solvent: "2nd fluid" (pH 6.8, 500 mL) as described in Japanese Pharmacopoeia 14th Edition, General Tests (disintegration test)

Temperature: 37° C.

Disk rotation speed: 50 rpm

Area of powder contacting with solvent on disk: 1 cm$^2$

Sampling amount: approx. 1 mL (HPLC conditions)

Column: YMC Pack ProC18 (YMC Co., Ltd.; inner diameter 4.6 mm, column length 150 mm, particle size 5 µm)

Column temperature: 40° C.

Flow rate: 1.0 mL/min

Mobile phase:
Solution A: $H_2O:CH_3CN:HClO_4=990:10:1$ (v/v/v)
Solution B: $CH_3CN:H_2O:HClO_4=900:100:1$ (v/v/v)
Concentration of solution B: 20%

Injection amount: 50 µL

Detection: ultraviolet absorbance photometer (wavelength: 252 nm)

Temperature of auto sampler: 25° C.

[Results]

Table 3 shows the dissolution rates.

TABLE 3

| | dissolution rate (µg/min/cm$^2$) |
|---|---|
| free form | 1.1 |
| mesylate amorphous | 22.7 |
| esylate amorphous | 25.1 |

For each amorphous form of the salts, the dissolution rate increased significantly in comparison to a crystalline form of the free form of the carboxamide.

INDUSTRIAL APPLICABILITY

The amorphous form of the salt of 4-(3-chloro-4-(cyclopropylaminocarbonyl)aminophenoxy)-7-methoxy-6-quinolinecarboxamide according to the invention is extremely useful as an angiogenesis inhibitor or a c-Kit kinase inhibitor.

What is claimed is:

1. An amorphous form of 4-(3-chloro-4-(cyclopropylaminocarbonyl)aminophenoxy)-7-methoxy-6-quinolinecarboxamide methanesulfonate having no noticeable peak in a powder X-ray diffraction.

2. An amorphous form of 4-(3-chloro-4-(cyclopropylaminocarbonyl)aminophenoxy)-7-methoxy-6-quinolinecarboxamide ethanesulfonate having no noticeable peak in a powder X-ray diffraction.

3. A process for preparing an amorphous form of 4-(3-chloro-4-(cyclopropylaminocarbonyl)aminophenoxy)-7-methoxy-6-quinolinecarboxamide methanesulfonate having no noticeable peak in a powder X-ray diffraction, said method comprising dissolving a crystalline form of 4-(3-chloro-4-(cyclopropylaminocarbonyl)aminophenoxy)-7-methoxy-6-quinolinecarboxamide methanesulfonate in an alcohol and water.

4. A process for preparing an amorphous form of 4-(3-chloro-4-(cyclopropylaminocarbonyl)aminophenoxy)-7-methoxy-6-quinolinecarboxamide ethanesulfonate having no noticeable peak in a powder X-ray diffraction, said method comprising dissolving a crystalline form of 4-(3-chloro-4-(cyclopropylaminocarbonyl)aminophenoxy)-7-methoxy-6-quinolinecarboxamide ethanesulfonate in an alcohol and water.

5. A pharmaceutical composition in the form of a tablet, powder, granule, capsule or lozenge, said pharmaceutical composition comprising the amorphous compound according to claim 1; and a pharmaceutically acceptable carrier.

6. A pharmaceutical composition in the form of a tablet, powder, granule, capsule or lozenge, said pharmaceutical composition comprising the amorphous compound according to claim 2; and a pharmaceutically acceptable carrier.

* * * * *